(12) United States Patent
Mahmoodian

(10) Patent No.: US 12,311,149 B2
(45) Date of Patent: *May 27, 2025

(54) FLUSH SYRINGE WITH FLIP CAP

(71) Applicant: Becton, Dickinson and Company, Franklin Lakes, NJ (US)

(72) Inventor: Roza Mahmoodian, New York, NY (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/581,629

(22) Filed: Feb. 20, 2024

(65) Prior Publication Data

US 2024/0189516 A1    Jun. 13, 2024

Related U.S. Application Data

(63) Continuation of application No. 17/386,770, filed on Jul. 28, 2021, now Pat. No. 11,944,792, which is a
(Continued)

(51) Int. Cl.
*A61M 5/31*    (2006.01)
*A61M 5/14*    (2006.01)
(Continued)

(52) U.S. Cl.
CPC ........ *A61M 5/3137* (2013.01); *A61M 5/3134* (2013.01); *A61M 2005/1403* (2013.01);
(Continued)

(58) Field of Classification Search
CPC .............. A61M 5/3137; A61M 5/3134; A61M 5/3148; A61M 5/31511;
(Continued)

(56) References Cited

U.S. PATENT DOCUMENTS 3,403,679 A    10/1968    Sinclair et al.
3,949,748 A    4/1976    Malmin
(Continued)

FOREIGN PATENT DOCUMENTS

CA    2803761 A1    12/2011
CA    2523133 C    2/2013
(Continued)

OTHER PUBLICATIONS

Final Office Action in U.S. Appl. No. 17/229,173 dated May 22, 2024, 28 pages.
(Continued)

*Primary Examiner* — Lauren P Farrar
(74) *Attorney, Agent, or Firm* — Servilla Whitney LLC

(57) ABSTRACT

Flush syringe assemblies are described herein. Such flush syringe assembly may include a barrel including a side wall defining a chamber, a collar mounted on a distal wall of the barrel and surrounding an elongate tip. A cap may be attached to the collar via a hinge. The flush syringe assembly may also include a cap attached to the collar via a hinge. A ring may be disposed around the collar with a locking element that engages with a corresponding mating locking projection on the cap. The cap may include a slanted surface. The slanted surface of the cap may include one or more ribs made of an elastomeric material.

18 Claims, 24 Drawing Sheets

Related U.S. Application Data continuation of application No. 16/253,683, filed on Jan. 22, 2019, now Pat. No. 11,083,847.

(60) Provisional application No. 62/622,517, filed on Jan. 26, 2018.

(51) Int. Cl.
 *A61M 5/315* (2006.01)
 *B65D 55/16* (2006.01)

(52) U.S. Cl.
 CPC ... *A61M 2005/3104* (2013.01); *A61M 5/3148* (2013.01); *A61M 5/31511* (2013.01); *A61M 2202/0478* (2013.01); *A61M 2205/586* (2013.01); *B65D 55/16* (2013.01)

(58) Field of Classification Search
 CPC .. A61M 2005/1403; A61M 2005/3104; A61M 2202/0478; A61M 2205/586
 See application file for complete search history.

(56) References Cited

U.S. PATENT DOCUMENTS

| | | | |
|---|---|---|---|
| 4,417,890 A | 11/1983 | Dennehey et al. |
| 4,444,335 A | 4/1984 | Wood et al. |
| 4,597,758 A | 7/1986 | Aalto et al. |
| D287,053 S | 12/1986 | Bucchianeri et al. |
| 4,642,102 A | 2/1987 | Ohmori |
| 4,711,363 A | 12/1987 | Marino |
| 4,738,376 A | 4/1988 | Markus |
| 4,795,432 A | 1/1989 | Karczmer |
| 4,813,940 A | 3/1989 | Parry |
| 4,906,231 A | 3/1990 | Young |
| 4,950,250 A | 8/1990 | Haber et al. |
| 5,084,017 A | 1/1992 | Maffetone |
| 5,259,840 A | 11/1993 | Boris |
| 5,395,347 A | 3/1995 | Blecher et al. |
| 5,478,311 A | 12/1995 | Klearman |
| 5,496,288 A | 3/1996 | Sweeney |
| 5,498,243 A | 3/1996 | Vallelunga et al. |
| 5,554,135 A | 9/1996 | Menyhay |
| 5,591,138 A | 1/1997 | Vaillancourt |
| 5,643,214 A | 7/1997 | Marshall et al. |
| 5,676,406 A | 10/1997 | Simmons et al. |
| 5,688,241 A | 11/1997 | Asbaghi |
| 5,755,696 A | 5/1998 | Caizza |
| D403,762 S | 1/1999 | Gabbard et al. |
| 5,984,123 A | 11/1999 | Mogami et al. |
| 5,984,899 A | 11/1999 | D'Alessio et al. |
| D420,129 S | 2/2000 | McMahon |
| RE36,885 E | 9/2000 | Blecher et al. |
| D432,231 S | 10/2000 | Balestracci |
| D437,050 S | 1/2001 | Balestracci |
| 6,176,846 B1 | 1/2001 | Balestracci |
| 6,183,448 B1 | 2/2001 | Mayer |
| D460,820 S | 7/2002 | Niedospial, Jr. |
| 6,419,656 B1 | 7/2002 | Vetter et al. |
| D461,243 S | 8/2002 | Niedospial, Jr. |
| 6,530,906 B2 | 3/2003 | Hu |
| 6,565,529 B1 | 5/2003 | Kimber et al. |
| 6,632,199 B1 | 10/2003 | Tucker et al. |
| 6,790,197 B2 | 9/2004 | Kosinski et al. |
| 6,884,237 B2 | 4/2005 | Asbaghi |
| 6,926,697 B2 | 8/2005 | Malenchek |
| 7,083,605 B2 | 8/2006 | Miyahara |
| 7,276,049 B2 | 10/2007 | Bang et al. |
| 7,361,159 B2 | 4/2008 | Fiser et al. |
| D570,476 S | 6/2008 | Sudo |
| D575,870 S | 8/2008 | Sudo |
| 7,513,888 B2 | 4/2009 | Sircom et al. |
| 7,686,784 B2 | 3/2010 | Baik |
| 7,811,261 B2 | 10/2010 | Rubinstein et al. |
| 8,012,131 B2 | 9/2011 | Moser et al. |
| 8,062,265 B2 | 11/2011 | Millerd |
| 8,162,882 B2 | 4/2012 | Rubinstein et al. |
| 8,303,541 B2 | 11/2012 | Chun |
| 8,333,738 B2 | 12/2012 | Millerd |
| 8,388,894 B2 | 3/2013 | Colantonio |
| 8,439,870 B2 | 5/2013 | Moyer et al. |
| 8,496,627 B2 | 7/2013 | Chelak et al. |
| 8,636,688 B2 | 1/2014 | Shaw |
| 8,636,703 B2 | 1/2014 | Foshee et al. |
| 8,647,307 B2 | 2/2014 | Gratwohl et al. |
| 8,647,308 B2 | 2/2014 | Solomon et al. |
| 8,663,129 B2 | 3/2014 | Allen et al. |
| 8,715,231 B2 | 5/2014 | Woehr |
| 8,721,627 B2 | 5/2014 | Alpert et al. |
| 8,747,355 B2 | 6/2014 | Rubinstein et al. |
| 8,777,504 B2 | 7/2014 | Shaw et al. |
| 8,784,388 B2 | 7/2014 | Charles et al. |
| 8,827,961 B2 | 9/2014 | Emmott et al. |
| 8,961,475 B2 | 2/2015 | Solomon et al. |
| 8,968,241 B2 | 3/2015 | Liversidge |
| 8,979,794 B2 | 3/2015 | Chevallier |
| 9,039,989 B2 | 3/2015 | Lui et al. |
| 9,050,416 B2 | 6/2015 | Feret et al. |
| 9,061,106 B2 | 6/2015 | Roberts et al. |
| 9,067,024 B2 | 6/2015 | Roberts et al. |
| 9,132,223 B1 | 9/2015 | Wakeel |
| 9,186,466 B2 | 11/2015 | Zachek et al. |
| 9,192,449 B2 | 11/2015 | Kerr et al. |
| 9,352,099 B2 | 5/2016 | Roberts et al. |
| 9,352,100 B2 | 5/2016 | Ward et al. |
| 9,352,101 B2 | 5/2016 | Roberts et al. |
| 9,370,327 B2 | 6/2016 | Teoh |
| 9,399,125 B2 | 7/2016 | Burkholz |
| 9,408,632 B2 | 8/2016 | Erskine |
| 9,445,760 B2 | 9/2016 | Allen et al. |
| 9,694,140 B2 | 7/2017 | Rubinstein et al. |
| 9,848,810 B2 | 12/2017 | Allen et al. |
| 10,099,048 B2 | 10/2018 | Chiu et al. |
| 10,166,381 B2 | 1/2019 | Gardner et al. |
| 10,376,686 B2 | 8/2019 | Burkholz et al. |
| 10,589,080 B2 | 3/2020 | Hitchcock et al. |
| 10,603,481 B2 | 3/2020 | Avula et al. |
| 10,871,246 B2 | 12/2020 | Marici et al. |
| 11,628,288 B1 | 4/2023 | Solomon et al. |
| 2002/0007147 A1 | 1/2002 | Capes et al. |
| 2003/0093009 A1 | 5/2003 | Newby et al. |
| 2003/0209681 A1 | 11/2003 | Leinsing et al. |
| 2004/0039341 A1 | 2/2004 | Ranalletta |
| 2004/0064105 A1 | 4/2004 | Capes et al. |
| 2004/0087910 A1 | 5/2004 | Nemoto |
| 2004/0186427 A1 | 9/2004 | Pok |
| 2004/0199113 A1 | 10/2004 | Capes et al. |
| 2004/0249348 A1 | 12/2004 | Wimpenny et al. |
| 2005/0038385 A1 | 2/2005 | Shen et al. |
| 2005/0065478 A1 | 3/2005 | Alheidt et al. |
| 2005/0147525 A1 | 7/2005 | Bousquet |
| 2005/0148932 A1 | 7/2005 | Rimlinger et al. |
| 2005/0187518 A1 | 8/2005 | Pelkey et al. |
| 2005/0197646 A1 | 9/2005 | Connell et al. |
| 2006/0052748 A1 | 3/2006 | Coelho et al. |
| 2006/0111668 A1 | 5/2006 | Baik |
| 2006/0167409 A1 | 7/2006 | Pelkey et al. |
| 2006/0247582 A1 | 11/2006 | Alheidt et al. |
| 2006/0258983 A1 | 11/2006 | Cirac Sole et al. |
| 2007/0005022 A1 | 1/2007 | Byrne et al. |
| 2007/0060904 A1 | 3/2007 | Vedrine et al. |
| 2007/0073225 A1 | 3/2007 | Lee et al. |
| 2007/0078406 A1 | 4/2007 | Lee |
| 2007/0129674 A1 | 6/2007 | Liversidge |
| 2007/0135764 A1 | 6/2007 | Chen |
| 2007/0179452 A1 | 8/2007 | Kosinski |
| 2007/0299395 A1 | 12/2007 | Pelkey et al. |
| 2008/0010766 A1 | 1/2008 | Kaufman et al. |
| 2008/0021414 A1 | 1/2008 | Alheidt |
| 2008/0033371 A1 | 2/2008 | Updegraff et al. |
| 2008/0171995 A1 | 7/2008 | Vitullo et al. |
| 2008/0177250 A1 | 7/2008 | Howlett et al. |
| 2008/0221531 A1 | 9/2008 | Alheidt et al. |
| 2008/0262439 A1 | 10/2008 | Alheidt |
| 2008/0300550 A1 | 12/2008 | Schiller et al. |

(56) References Cited

U.S. PATENT DOCUMENTS

| | | |
|---|---|---|
| 2008/0300551 A1 | 12/2008 | Schiller et al. |
| 2009/0008393 A1 | 1/2009 | Howlett et al. |
| 2009/0048560 A1 | 2/2009 | Caizza et al. |
| 2009/0062736 A1 | 3/2009 | Jan |
| 2009/0062766 A1 | 3/2009 | Howlett et al. |
| 2009/0076450 A1 | 3/2009 | Caizza et al. |
| 2009/0088724 A1 | 4/2009 | Chebator et al. |
| 2009/0093793 A1 | 4/2009 | Gross et al. |
| 2009/0171285 A1 | 7/2009 | Wang |
| 2009/0177156 A1 | 7/2009 | MacLean |
| 2009/0205151 A1 | 8/2009 | Fisher et al. |
| 2009/0287161 A1 | 11/2009 | Traub et al. |
| 2009/0318880 A1 | 12/2009 | Janish |
| 2010/0000040 A1 | 1/2010 | Shaw et al. |
| 2010/0049170 A1 | 2/2010 | Solomon et al. |
| 2010/0050351 A1 | 3/2010 | Colantonio et al. |
| 2010/0076370 A1 | 3/2010 | Howlett et al. |
| 2010/0100056 A1 | 4/2010 | Cawthon et al. |
| 2010/0174236 A1 | 7/2010 | Burns et al. |
| 2010/0274190 A1 | 10/2010 | Wayman et al. |
| 2010/0286609 A1 | 11/2010 | Mahurkar |
| 2010/0286610 A1 | 11/2010 | Chang |
| 2010/0298770 A1 | 11/2010 | Rubinstein et al. |
| 2011/0046603 A1 | 2/2011 | Felsovalyi et al. |
| 2011/0054440 A1 | 3/2011 | Lewis |
| 2011/0264037 A1 | 10/2011 | Foshee et al. |
| 2012/0039764 A1 | 2/2012 | Solomon et al. |
| 2012/0109073 A1 | 5/2012 | Anderson et al. |
| 2012/0111368 A1 | 5/2012 | Rahimy et al. |
| 2012/0123386 A1 | 5/2012 | Tsals |
| 2012/0265163 A1 | 10/2012 | Cheng et al. |
| 2012/0302997 A1 | 11/2012 | Gardner et al. |
| 2013/0085474 A1 | 4/2013 | Charles et al. |
| 2013/0171030 A1 | 7/2013 | Ferlic et al. |
| 2013/0197485 A1 | 8/2013 | Gardner et al. |
| 2013/0218097 A1 | 8/2013 | Alheidt et al. |
| 2013/0338644 A1 | 12/2013 | Solomon et al. |
| 2014/0052074 A1 | 2/2014 | Tekeste |
| 2014/0135706 A1 | 5/2014 | Rubinstein et al. |
| 2014/0148781 A1 | 5/2014 | Tekeste |
| 2014/0150832 A1 | 6/2014 | Rogers et al. |
| 2014/0228772 A1 | 8/2014 | Ward et al. |
| 2014/0364803 A1 | 12/2014 | Rubinstein et al. |
| 2014/0366914 A1 | 12/2014 | Kerr et al. |
| 2015/0011936 A1 | 1/2015 | Okihara et al. |
| 2015/0094659 A1 | 4/2015 | Schraga |
| 2015/0094666 A1 | 4/2015 | Bates et al. |
| 2015/0182704 A1 | 7/2015 | Chevallier |
| 2015/0190580 A1 | 7/2015 | Imai et al. |
| 2015/0190586 A1 | 7/2015 | Takemoto |
| 2015/0374968 A1 | 12/2015 | Solomon et al. |
| 2016/0045629 A1 | 2/2016 | Gardner et al. |
| 2016/0067422 A1 | 3/2016 | Davis et al. |
| 2016/0101276 A1 | 4/2016 | Tekeste |
| 2016/0158520 A1 | 6/2016 | Ma et al. |
| 2017/0203092 A1 | 7/2017 | Ryan et al. |
| 2018/0085568 A1 | 3/2018 | Drmanovic |
| 2018/0200145 A1 | 7/2018 | Sanders et al. |
| 2018/0200500 A1 | 7/2018 | Ziebol et al. |
| 2018/0214684 A1 | 8/2018 | Avula et al. |
| 2018/0237190 A1 | 8/2018 | Iwasaki |
| 2018/0243547 A1 | 8/2018 | Fox et al. |
| 2018/0256879 A1 | 9/2018 | Chiu et al. |
| 2018/0256883 A1 | 9/2018 | Follman et al. |
| 2019/0000115 A1 | 1/2019 | Ma et al. |
| 2019/0001115 A1 | 1/2019 | Ma et al. |
| 2019/0151643 A1 | 5/2019 | Alpert |
| 2019/0232039 A1 | 8/2019 | Erekovcanski et al. |
| 2019/0234540 A1 | 8/2019 | Marici et al. |
| 2019/0308006 A1 | 10/2019 | Erekovcanski et al. |
| 2019/0351212 A1 | 11/2019 | Dudar et al. |
| 2020/0147360 A1 | 5/2020 | Arnett et al. |
| 2021/0100996 A1 | 4/2021 | Wijesuriya et al. |
| 2021/0187267 A1 | 6/2021 | Jiang |

FOREIGN PATENT DOCUMENTS

| | | |
|---|---|---|
| CH | 518102 | 1/1972 |
| CN | 1322119 A | 11/2001 |
| CN | 1771066 A | 5/2006 |
| CN | 1874815 A | 12/2006 |
| CN | 101541361 A | 9/2009 |
| CN | 101631585 A | 1/2010 |
| CN | 101980746 A | 2/2011 |
| CN | 201807018 U | 4/2011 |
| CN | 102188766 A | 9/2011 |
| CN | 102448502 A | 5/2012 |
| CN | 103025374 A | 4/2013 |
| CN | 103079610 A | 5/2013 |
| CN | 103083767 A | 5/2013 |
| CN | 204161736 U | 2/2015 |
| CN | 206198472 U | 5/2017 |
| CN | 206315311 U | 7/2017 |
| CN | 213852498 U | 8/2021 |
| CN | 214388299 U | 10/2021 |
| CN | 216022674 U | 3/2022 |
| DE | 20017013 U1 | 12/2000 |
| DE | 10247963 A1 | 5/2004 |
| DE | 202005004079 U1 | 7/2006 |
| EP | 0589379 A1 | 3/1994 |
| EP | 0627231 C | 12/1994 |
| EP | 2606930 A1 | 6/2013 |
| EP | 2585146 B1 | 3/2017 |
| EP | 2832391 B1 | 1/2018 |
| EP | 3275490 A1 | 1/2018 |
| GB | 622848 C | 5/1949 |
| GB | 2408259 A | 5/2005 |
| GB | 2518646 A | 4/2015 |
| JP | H03139363 A | 6/1991 |
| JP | H04501672 A | 3/1992 |
| JP | 2001502191 A | 2/2001 |
| JP | 2001521792 A | 11/2001 |
| JP | 2004504895 A | 2/2004 |
| JP | 2004208740 A | 7/2004 |
| JP | 2006501944 A | 1/2006 |
| JP | 2006507062 A | 3/2006 |
| JP | 2008119075 A | 5/2008 |
| JP | 2008526363 B2 | 7/2008 |
| JP | 2008532701 A | 8/2008 |
| JP | 2008239164 A | 10/2008 |
| JP | 2008253775 A | 10/2008 |
| JP | 2009028527 A | 2/2009 |
| JP | 2009082715 A | 4/2009 |
| JP | 2009106687 A | 5/2009 |
| JP | 2009526241 A | 7/2009 |
| JP | 2010527276 A | 8/2010 |
| JP | 2013509274 A | 3/2013 |
| JP | 2013529973 A | 7/2013 |
| JP | 2013530794 A | 8/2013 |
| JP | 2014532517 A | 12/2014 |
| JP | 2015517377 A | 6/2015 |
| JP | 2016511119 A | 4/2016 |
| JP | 2016104214 A | 6/2016 |
| JP | 2017534351 A | 11/2017 |
| MX | 2013/000081 | 3/2013 |
| MX | 349289 B | 7/2017 |
| WO | 200024442 A1 | 5/2000 |
| WO | 200224551 A1 | 3/2002 |
| WO | 2011066586 A1 | 6/2011 |
| WO | 2012013587 A1 | 2/2012 |
| WO | 2012144026 A1 | 10/2012 |
| WO | 2013046857 A1 | 4/2013 |
| WO | 2014159346 A1 | 10/2014 |
| WO | 2015121602 A1 | 8/2015 |
| WO | 2015127285 A1 | 8/2015 |
| WO | 2015174953 A1 | 11/2015 |
| WO | 2016158144 A1 | 10/2016 |
| WO | 2017087400 A1 | 5/2017 |
| WO | 2017095373 A1 | 6/2017 |
| WO | 2018106508 A1 | 6/2018 |
| WO | 2018237090 A1 | 12/2018 |
| WO | 2019147906 A1 | 8/2019 |
| WO | 2019152482 A1 | 8/2019 |

(56) References Cited

FOREIGN PATENT DOCUMENTS

| WO | 2019212637 A1 | 11/2019 |
| WO | 2020056120 A1 | 3/2020 |
| WO | 2020112767 A1 | 6/2020 |

OTHER PUBLICATIONS

Non-Final Office Action in U.S. Appl. No. 17/992,169 dated May 8, 2024, 13 pages.
"Ruhof Dry Sponges", Ruhof, Sep. 30, 2016, https://www.ruhof.com/products/ruhof-dry-sponges (Year: 2016).
"Final Office Action in U.S. Appl. No. 12/833,551 dated Dec. 26, 2012, 9 pages".
"Final Office Action in U.S. Appl. No. 13/871,682 dated Dec. 1, 2014, 10 pages".
"Final Office Action in U.S. Appl. No. 16/253,683 dated Dec. 23, 2020, 9 pages".
"Final Office Action in U.S. Appl. No. 16/254,747 dated Jan. 22, 2021, 16 pages".
"International Search Report in PCT/US2019/015789, mailed Apr. 16, 2019, 12 pages".
"Non-Final Office Action in S/N 121833,432 mailed Mar. 30, 2012, 9 pgs."
"Non-Final Office Action in U.S. Appl. No. 13/871,682 dated May 9, 2014, 8 pages".
"Non-Final Office Action in U.S. Appl. No. 15/864,185 dated Nov. 28, 2014, 6 pages".
"Non-Final Office Action in U.S. Appl. No. 16/253,683, mailed on Jun. 26, 2020, 9 pages".
"Non-Final Office Action in U.S. Appl. No. 16/254,747, mailed on Aug. 20, 2020, 14 pages".
"Non-Final Office Action in U.S. Appl. No. 16/378,015, mailed on Oct. 30, 2020, 18 pages".
"Non-Final Office Action in U.S. Appl. No. 16/838,461, mailed on Jul. 24, 2020, 10 pages".
"PCT International Search Report and Written Opinion in PCT/US2017/065956 dated Mar. 5, 2018, 14 pages".
"PCT International Search Report and Written Opinion in PCT/US2019/015096 dated Mar. 21, 2019, 12 pages".
"PCT International Search Report and Written Opinion in PCT/US2019/015100 dated Apr. 10, 2019, 10 pages".
"PCT International Search Report and Written Opinion in PCT/US2019/026482 dated Jul. 30, 2019, 13 pages".
"PCT International Search Report and Written Opinion in PCT/US2020/015535 dated May 4, 2020, 13 pages".
"PCT International Search Report and Written Opinion in PCT/US2020/041097 dated Oct. 28, 2020, 18 pages".
"PCT International Search Report and Written Opinion in PCT/US2020/041311 dated Sep. 30, 2020, 16 pages".
"PCT International Search Report and Written Opinion in PCT/US2020/041312 dated Oct. 19, 2020, 11 pages".
"PCT International Search Report and Written Opinion in PCT/US2020/044942 dated Oct. 16, 2020, 15 pages".
"PCT International Search Report and Written Opinion in PCT/US2020/044951 dated Oct. 14, 2020, 14 pages".
"PCT International Search Report and Written Opinion in PCT/US2020/057611 dated Feb. 5, 2021, 11 pages".
"PCT International Search Report and Written Opinion in PCT/US2020/065228 dated Mar. 29, 2021, 12 pages".
"PCT International Search Report and Written Opinion in PCT/US2020/065229 dated Mar. 29, 2021, 11 pages".
"PCT International Search Report and Written Opinion in PCT/US2021/027214 dated Jul. 19, 2021, 14 pages".
"PCT International Search Report and Written Opinion in PCT/US2021/027218 dated Jul. 22, 2021, 14 pages".
"PCT International Search Report and Written Opinion in PCT/US2021/027219 dated Oct. 22, 2021, 22 pages".
"PCT International Search Report and Written Opinion in PCT/US2021/027220 dated Jul. 21, 2021, 15 pages".

FLUSH SYRINGE WITH FLIP CAP

CROSS-REFERENCE TO RELATED APPLICATIONS

This application is a continuation of U.S. application Ser. No. 17/386,770, filed on Jul. 28, 2021, now allowed, which is a continuation of U.S. application Ser. No. 16/253,683, filed on Jan. 22, 2019, now issued as U.S. Pat. No. 11,083,847 on Aug. 10, 2021 which claims priority under 35 U.S.C. § 119(c) to U.S. Provisional Application No. 62/622,517, filed Jan. 26, 2018, the disclosures of which are incorporated herein by reference in their entirety.

TECHNICAL FIELD

The present disclosure generally relates to syringe assemblies, and particularly to syringe assemblies comprising a physical barrier to prevent contact of the syringe tip with the surrounding non-sterile environment. Embodiments of the present disclosure ensure adherence to aseptic techniques for use in flush procedures for vascular access devices (VAD's). Embodiments of the present disclosure are also directed to technology to reduce the risk for bloodstream infections (CRBSI) and intravenous (IV) line patency maintenance including capping technology, particularly for syringe assemblies to allow for one-handed removal of a syringe cap for use in flush procedures.

BACKGROUND

Vascular access devices (VADs) are commonly used therapeutic devices, which include peripheral catheters and central venous catheters. If not properly maintained or if exposed to a non-sterile environment, the VADs can become contaminated, sealed with blood clots or spread infection. To ensure VADs are used properly and do not become sealed or infected, protocols to ensure sterile practice have been developed. These protocols include sterilizing the VAD and flushing the catheter with a flush solution. Catheters are flushed using syringe assemblies filled with various fluids. In some cases, different fluids are injected sequentially in accordance with the protocol. For example, a saline solution followed by an anticoagulant such as heparin. The size of the syringe used to flush intravenous (I.V.) lines varies by various factors including the size and length of the catheter. Typically syringes of 1 ml, 3 ml, 5 ml and 10 ml volume are used. VAD protocols usually recommend flush procedures be performed after catheter placement, before fluid infusion, and before and after drug administration, blood sampling, transfusions and parenteral nutrition. The goal of these flush procedures is to confirm catheter patency, avoid drug incompatibilities, ensure the complete drug dose administration, prevent thrombus formation and minimize the risk of blood stream infections.

Currently existing pre-filled syringes have syringe tip caps that require two hands for holding the syringe and cap removal. Conventional flush syringes have a barrel with a luer tip at one end which is exposed to the non-sterile environment once the syringe tip is removed from packaging thus providing an opportunity for undesired contamination. Consequently, there is a need for a syringe, particularly a flush syringe, providing a physical barrier around the syringe tip which promotes aseptic practice by reducing or eliminating "touch" contamination of the syringe, particularly the tip of a syringe, with the surrounding non-sterile environment. There is also a need for a syringe, particularly a flush syringe, which allows the clinician to open a protective cap with one hand, without the hand being in close proximity of the syringe tip. In addition to enhanced safety, such a one-handed operation would greatly improve workflow and efficiency.

SUMMARY

One aspect of the present disclosure pertains to a flush syringe assembly including aa barrel having a side wall having an inside surface defining a chamber for retaining a fluid, an open proximal end, a distal end including a distal wall with an elongate tip extending distally therefrom having a passageway therethrough in fluid communication with said chamber. A collar may be mounted on the distal wall of the barrel and surrounds the elongate tip. The collar includes at least one side wall having an inside surface defining a compartment, an open distal end, a proximal end adjacent the distal wall of the barrel. A cap may be attached to the collar via a hinge. An elongated plunger rod disposed within the barrel, the plunger rod including a distal end and a proximal end, the distal end including a stopper slidably positioned in fluid-tight engagement with the inside surface of the barrel for drawing fluid into and driving fluid out of the chamber by movement of the stopper relative to the barrel. The elongated plunger rod extending outwardly from the open proximal end of the barrel and the stopper has a distal surface.

In one or more embodiments, the compartment of the collar surrounds the elongated tip.

In one or more embodiments, the hinge is a living hinge.

In one or more alternate embodiments, the hinge is a butterfly shape with a central hinge section and two lateral wings.

In one or more alternate embodiments, the hinge is spring loaded.

In one or more alternate embodiments, the hinge opens between a fully closed position to a fully open position of at least 120 degrees.

In one or more alternate embodiments, the cap includes an outwardly extending protrusion that interacts with the elongate tip.

In one or more embodiments, the protrusion may be button-shaped, pin-shaped, or umbrella-shaped.

In one or more embodiments, a gasket may be disposed between the collar and the cap.

In one or more embodiments, the locking element is the form of an arm.

In one or more embodiments, the cap includes a slanted surface. In one or more embodiments, the slanted surface may include one or more ribs. The one or more ribs may be made of an elastomeric material.

Another aspect of the present disclosure pertains to a flush syringe assembly including a barrel including a side wall having an inside surface defining a chamber for retaining a fluid, an open proximal end, a distal end including a distal wall with an elongate tip extending distally therefrom having a passageway therethrough in fluid communication with said chamber. A collar may be mounted on the distal wall of the barrel and surrounding the elongate tip, the collar including at least one side wall having an inside surface defining a compartment, an open distal end, a proximal end adjacent the distal wall of the barrel. In one or more embodiments, a cap may be attached to the collar via a hinge. In one or more embodiments, a ring is disposed around the collar with a locking element that engages with a corresponding mating locking projection on the cap. In one or more embodiments, an elongated plunger rod disposed within the barrel, the plunger rod comprising a distal end and a proximal end, the distal end including a stopper slidably positioned in fluid-tight engagement with the inside surface of the barrel for drawing fluid into and driving fluid out of the chamber by movement of the stopper relative to the barrel, the elongated plunger rod extending outwardly from the open proximal end of the barrel.

In one or more embodiments, the ring may be turned to disengage the locking element from mating locking projection on the cap. In one or more embodiments, the ring includes one or more thumb supports. In one or more embodiments, the locking element is the form of an arm.

In one or more embodiments, the cap includes a slanted surface.

DETAILED DESCRIPTION

Figure 1:
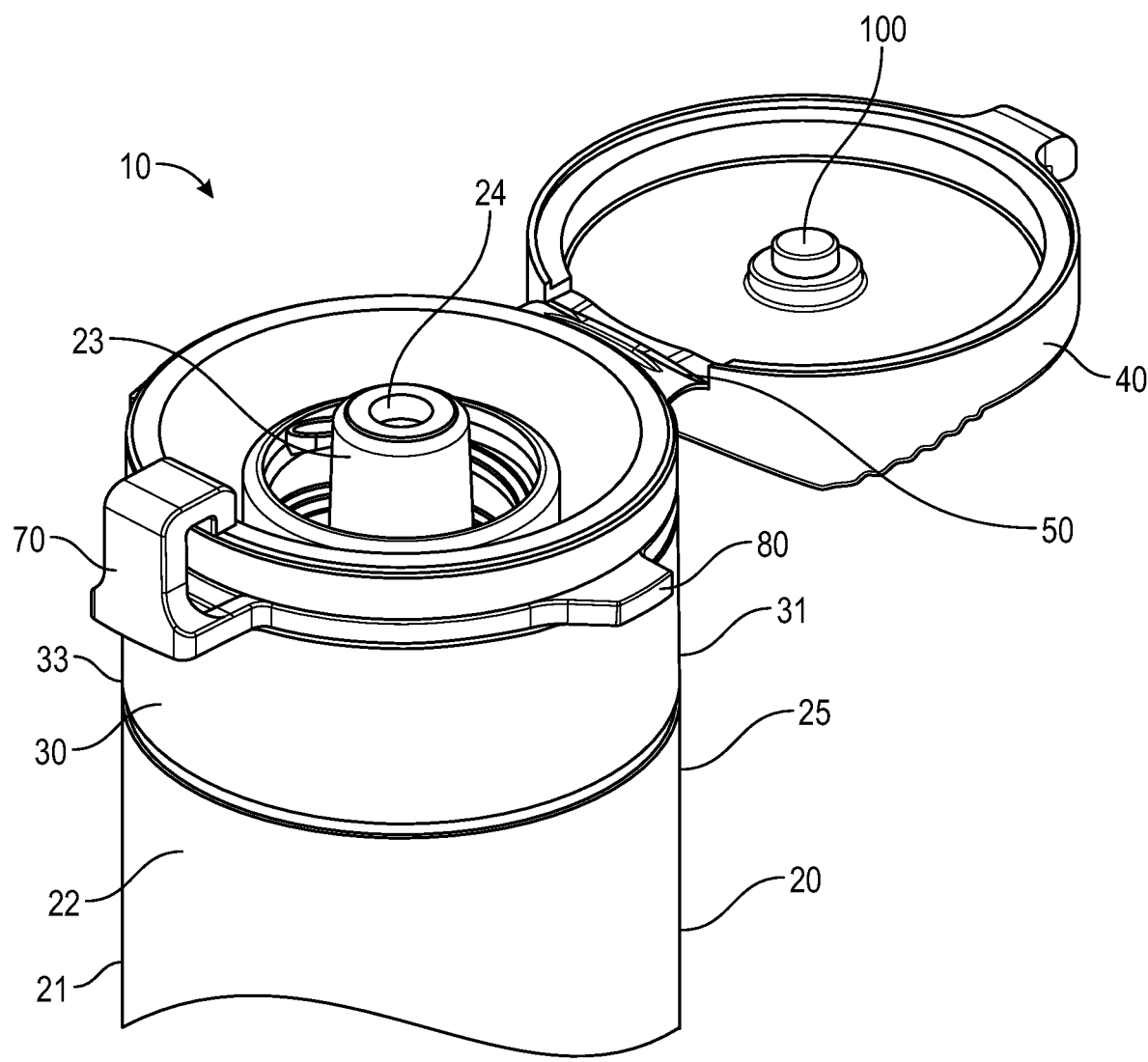
FIG. 1 illustrates a perspective view of a flush syringe with a flip cap and locking element in an open position in accordance with one or more embodiments of the present disclosure.

Before describing several exemplary embodiments of the present disclosure, it is to be understood that the disclosure is not limited to the details of construction or process steps set forth in the following description. The disclosure is capable of other embodiments and of being practiced or being carried out in various ways.

With respect to terms used in this disclosure, the following definitions are provided.

Reference to "flush syringe assembly" includes syringes that are indicated for use in the flushing of VADs. The practice of flushing ensures and maintains catheter patency and helps prevent the mixing of incompatible pharmaceuticals.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the VAD. A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

Clinicians need to handle multiple components while accessing an intravenous (IV) line or catheter: open and disinfect the hub, open the syringe, hold the line in place, etc. while ensuring that none of the devices touch any surfaces as this would lead to contamination and blood stream infections which can have deadly outcomes. Thus accessing an intravenous (IV) line or catheter is not straightforward and requires a certain level of dexterity to carry out the procedure while preventing the syringe tip from coming into contact with the surrounding environment. If the syringe tip touches any non-sterile surfaces, "touch" contamination can occur which can cause microbial growth in the IV line and consequently lead to incidents of catheter-associated-bloodstream infection ("CRBSI") and central line-associated bloodstream infection ("CLABSI") which are very costly and lethal.

Embodiments of the present disclosure relate to a flush syringe having a collar and a hinged cap surrounding the elongate tip of the syringe. The collar provides a physical barrier around the syringe tip. Because of its shape, the collar of the present disclosure can help facilitate the alignment of the flush syringe with the catheter hub and/or needle-free connector and thus reduce the chances of "touch" contamination. Embodiments of the present disclosure protect the syringe tip while currently available syringes leave the syringe tip fully exposed once a protective tip cap is removed, and therefore leaving the syringe tip prone to touch contamination. Embodiments of the present disclosure having an incorporated elevated collar surrounding the syringe tip enable case of alignment of luer tips in devices such as needleless connectors and prefilled syringes, which can be very small, while also allowing for prevention of touch contamination. Absent the embodiments of the present disclosure, alignment of luer tips require careful attention and visual precision for being able to align the two parts perfectly such that no contamination occurs.

Referring to FIGS. 1-13, a syringe assembly 10 according to the present disclosure generally comprises a barrel 20, including a side wall 21 having an inside surface defining a chamber 22 for retaining a fluid. In one or more embodiments, the fluid is a flush fluid. The barrel 20 further includes an open proximal end and a distal end having a distal wall with an elongated tip 23 extending distally therefrom and having a passageway 24 therethrough in fluid communication with the chamber, the distal wall adapted for connection to a collar 30.

Figure 2:
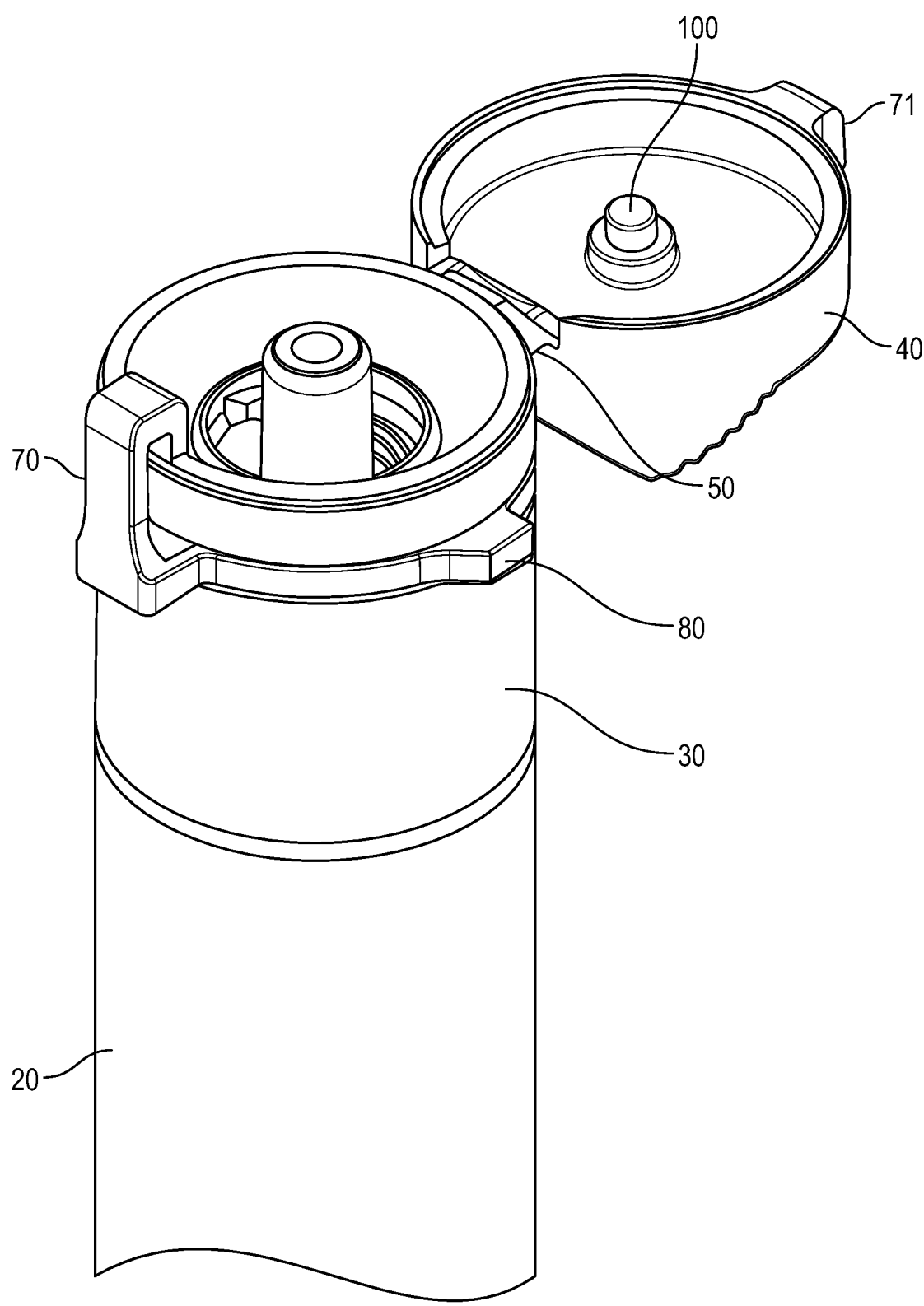
FIG. 2 illustrates a perspective view of a flush syringe with a flip cap and locking element in an open position in accordance with one or more embodiments of the present disclosure.
Figure 3:
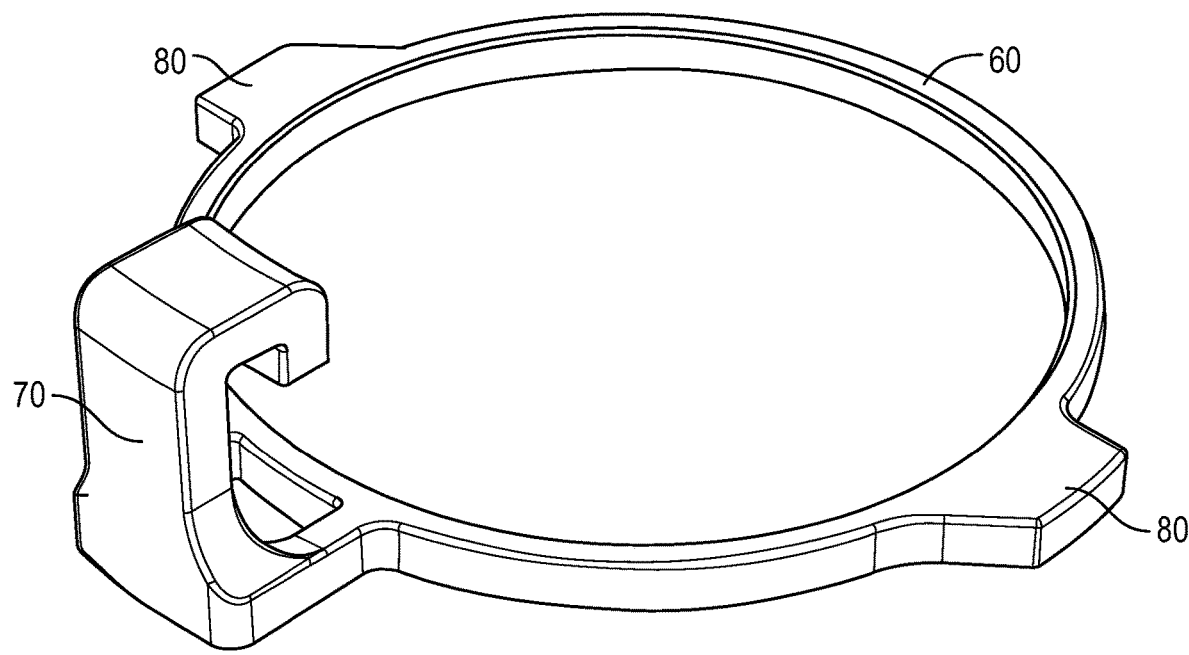
FIG. 3 illustrates a perspective view of a ring with locking element and turn tab in accordance with one or more embodiments of the present disclosure.
Figure 4:
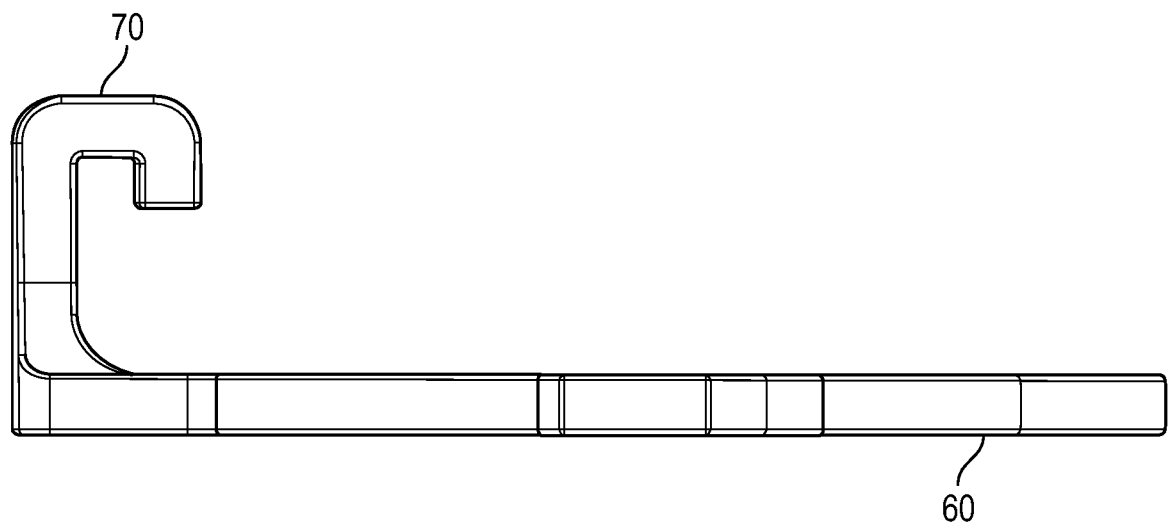
FIG. 4 illustrates a side view of a ring of FIG. 3 in accordance with one or more embodiments of the present disclosure.
Figure 5:
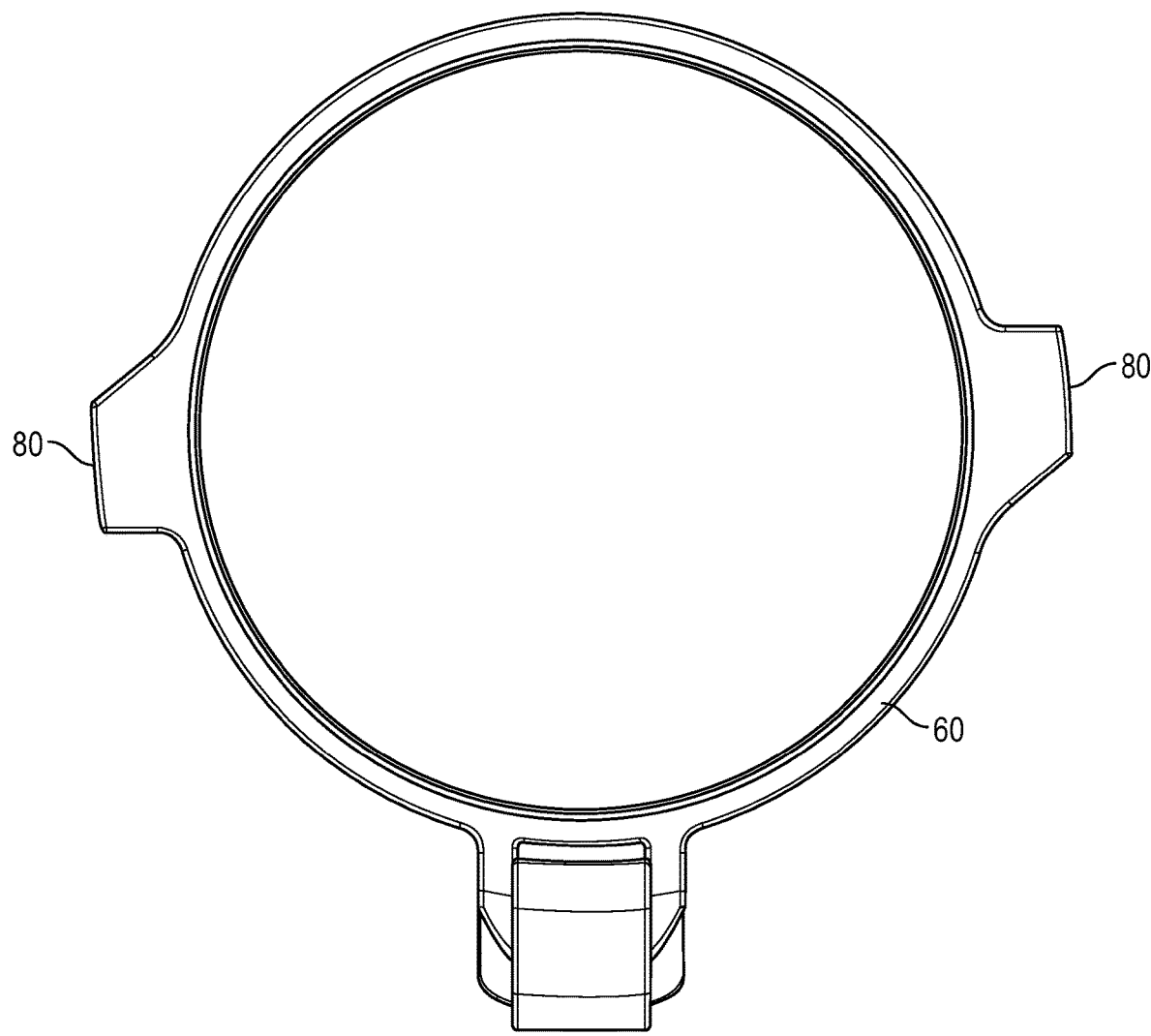
FIG. 5 illustrates a top a ring of FIG. 3 in accordance with one or more embodiments of the present disclosure.

As shown in FIG. 2, collar 30 mounted on the distal end of the barrel 20, the collar 30 including at least one side wall 31 having an inside surface defining a compartment surrounding the elongated tip 23, a open distal end 32, and a proximal end 33 adjacent the distal wall 25 of the barrel. Elongated tip 23 adapted for connection to a hub of a vascular access device. As shown in FIG. 2, the inner surface of cap 40 has a protrusion in the form of a button to block off a corresponding luer tip to prevent fluid leakage inside the cap area when closed, In one or more embodiments, the collar 30 is an elevated collar around the elongated tip 23. In one or more embodiments, the collar 30 is an extension of the barrel 20. Collar 30 aids in aligning the elongated tip 23 to other luer devices, such as needleless connectors, and protects the elongated tip from touch contamination.

In one or more embodiments, as shown in FIGS. 3-5 and 13, the collar 30 has a ring 60 around the collar 30 with a locking element 70 that engages with its corresponding mating locking projection 71 on the cap 40. The collar is turned to disengage the locking element 70 from corresponding mating locking projection 71 on the cap 40 to prepare the cap to be flipped open. In one or more embodiments, there are two thumb supports 80 for turning the collar—one for left handed clinicians and one for right handed clinicians.

Figure 6:
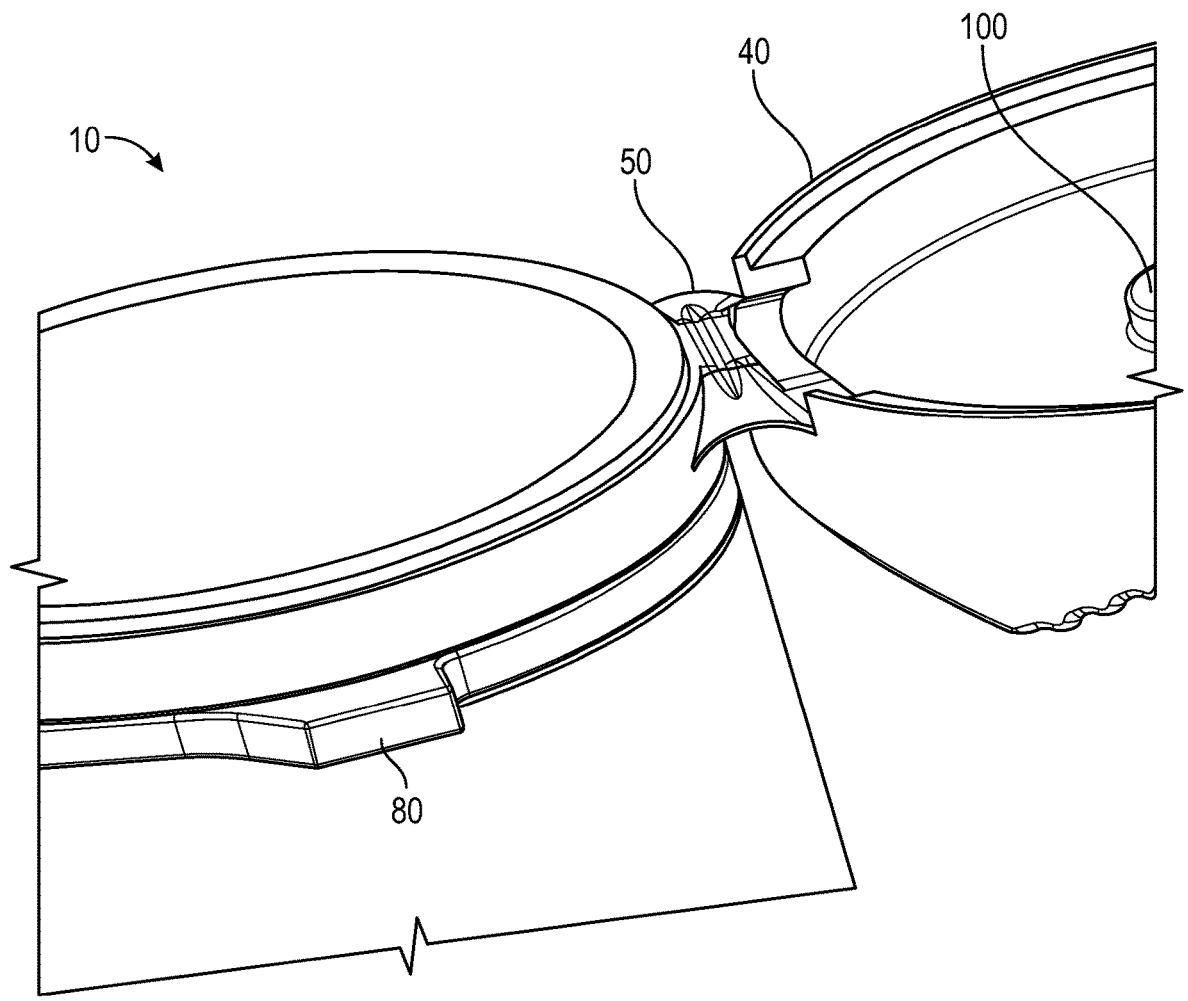
FIG. 6 illustrates a partial perspective view of a flush syringe with a hinge connecting the collar and cap in accordance with one or more embodiments of the present disclosure.
Figure 7:
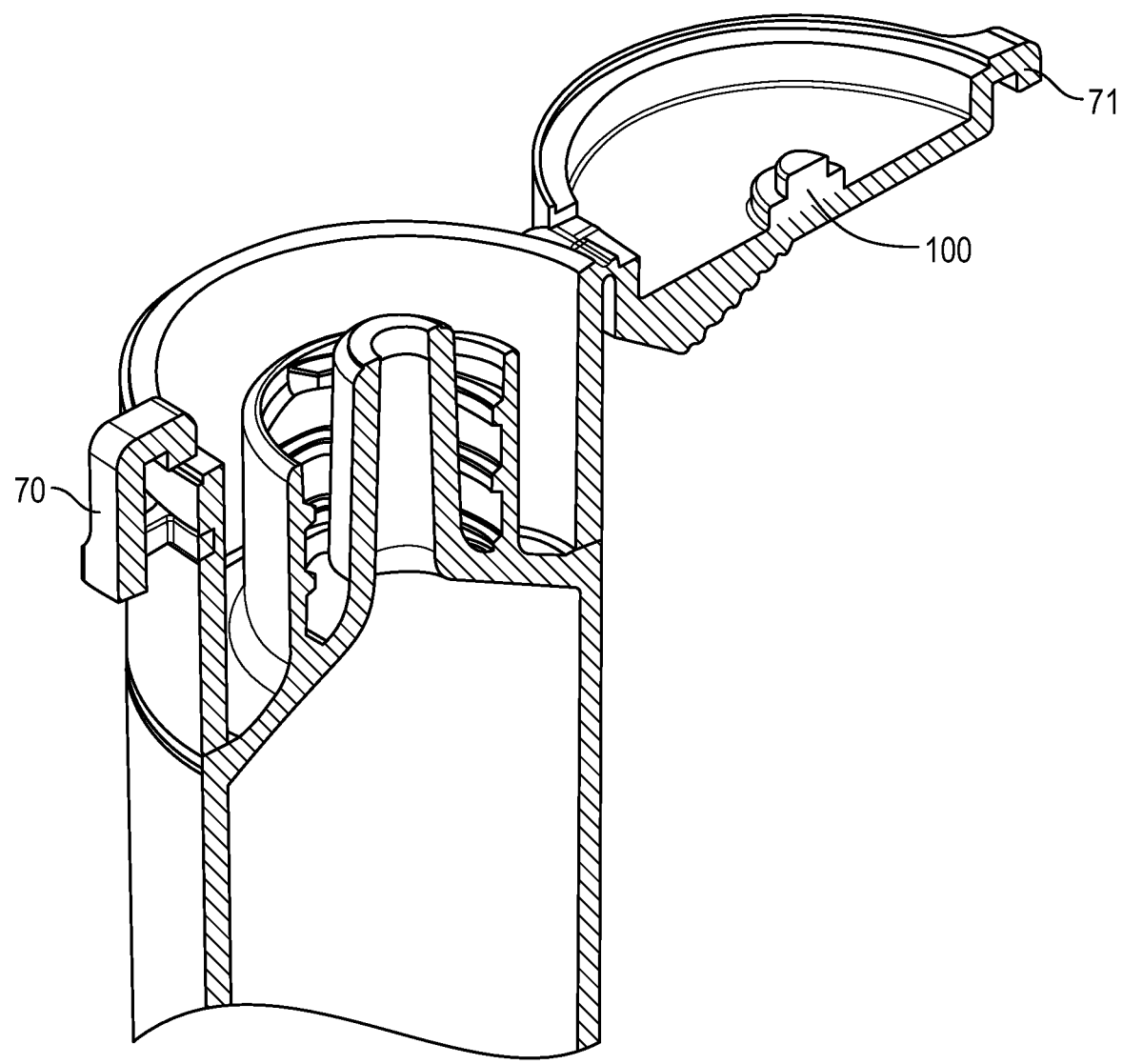
FIG. 7 illustrates a cross-sectional perspective view of a flush syringe with a collar and a cap in accordance with one or more embodiments of the present disclosure.
Figure 8:
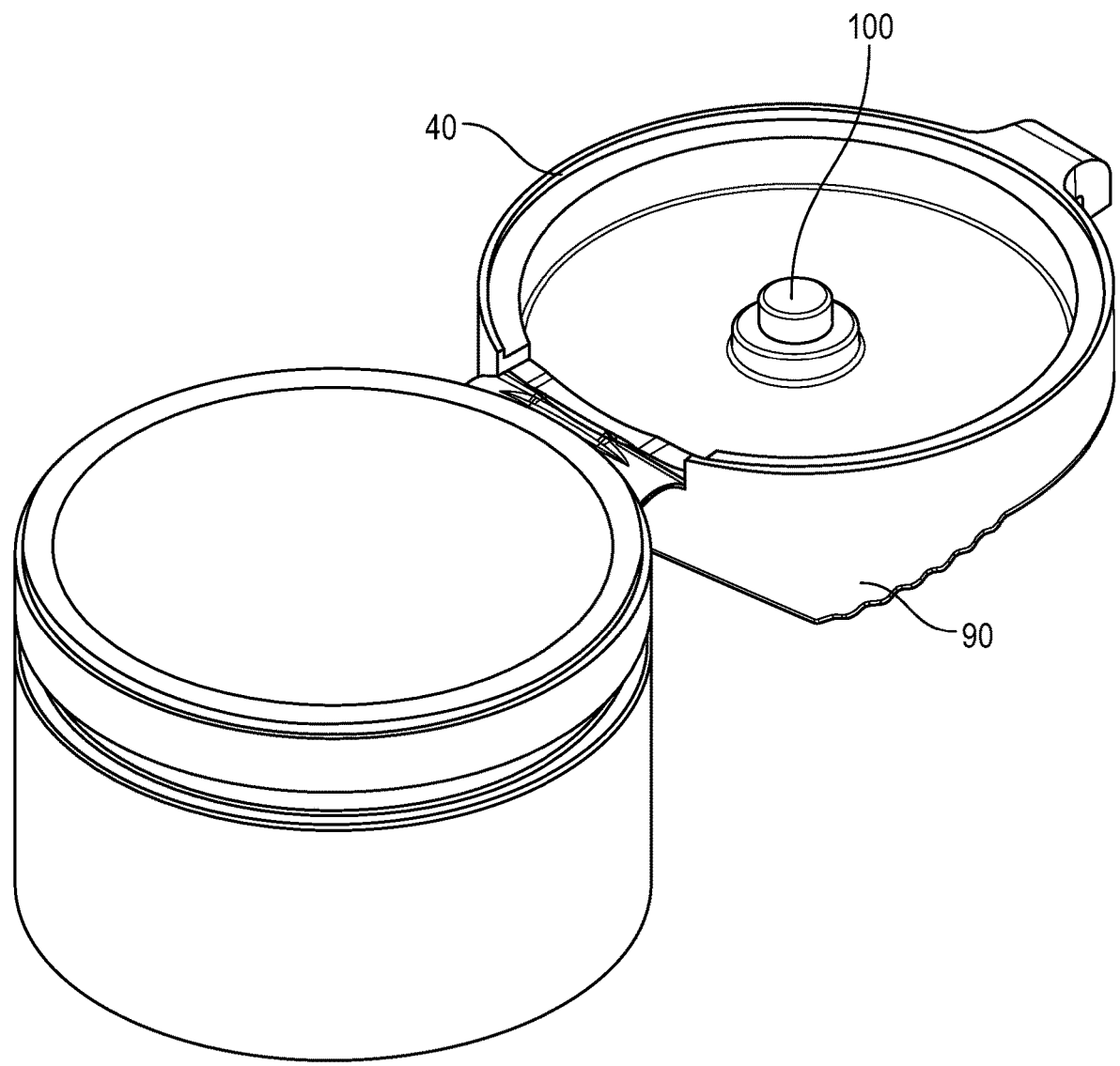
FIG. 8 illustrates a partial perspective view of a collar and a cap with sealing protrusion in the shape of a button and locking element in accordance with one or more embodiments of the present disclosure.
Figure 9:
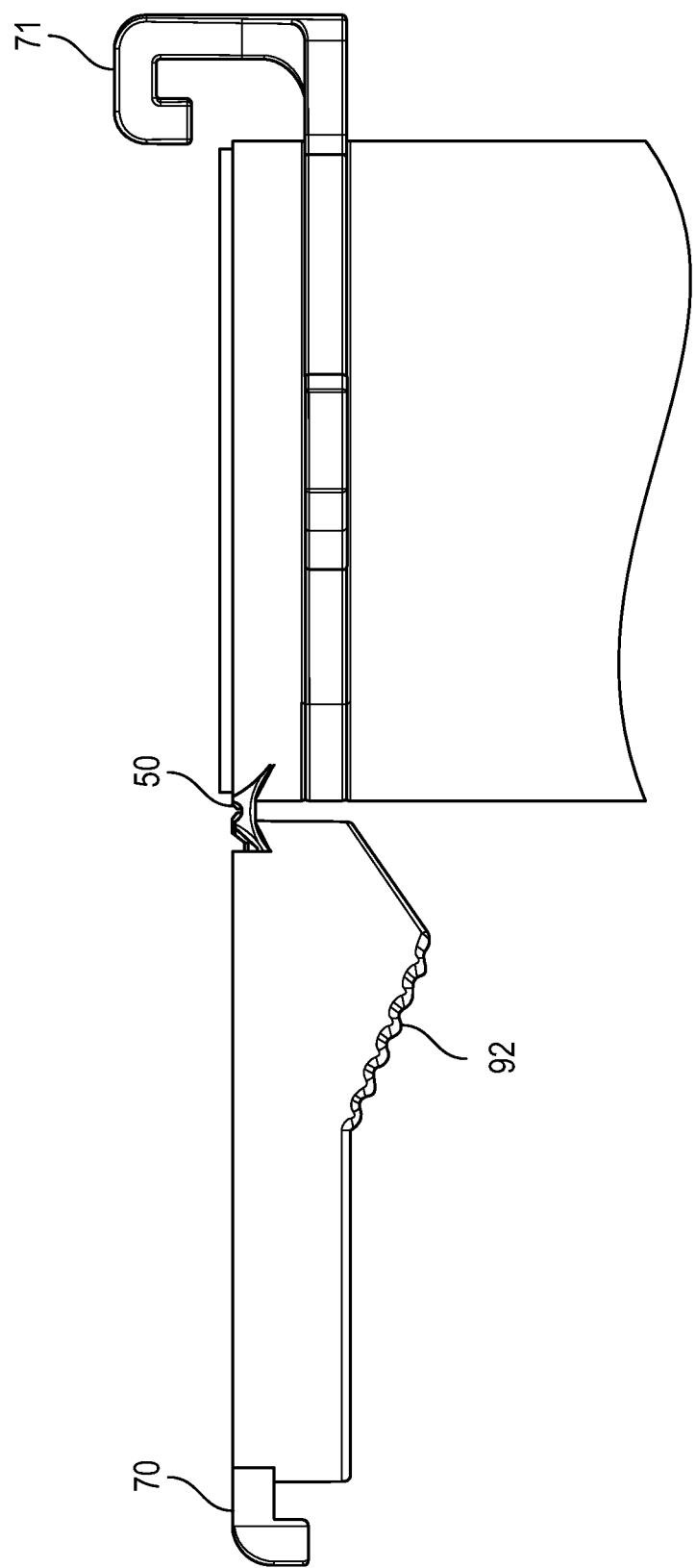
FIG. 9 illustrates a side view of a syringe assembly with a collar, a ring and a cap in an open position in accordance with one or more embodiments of the present disclosure.
Figure 10:
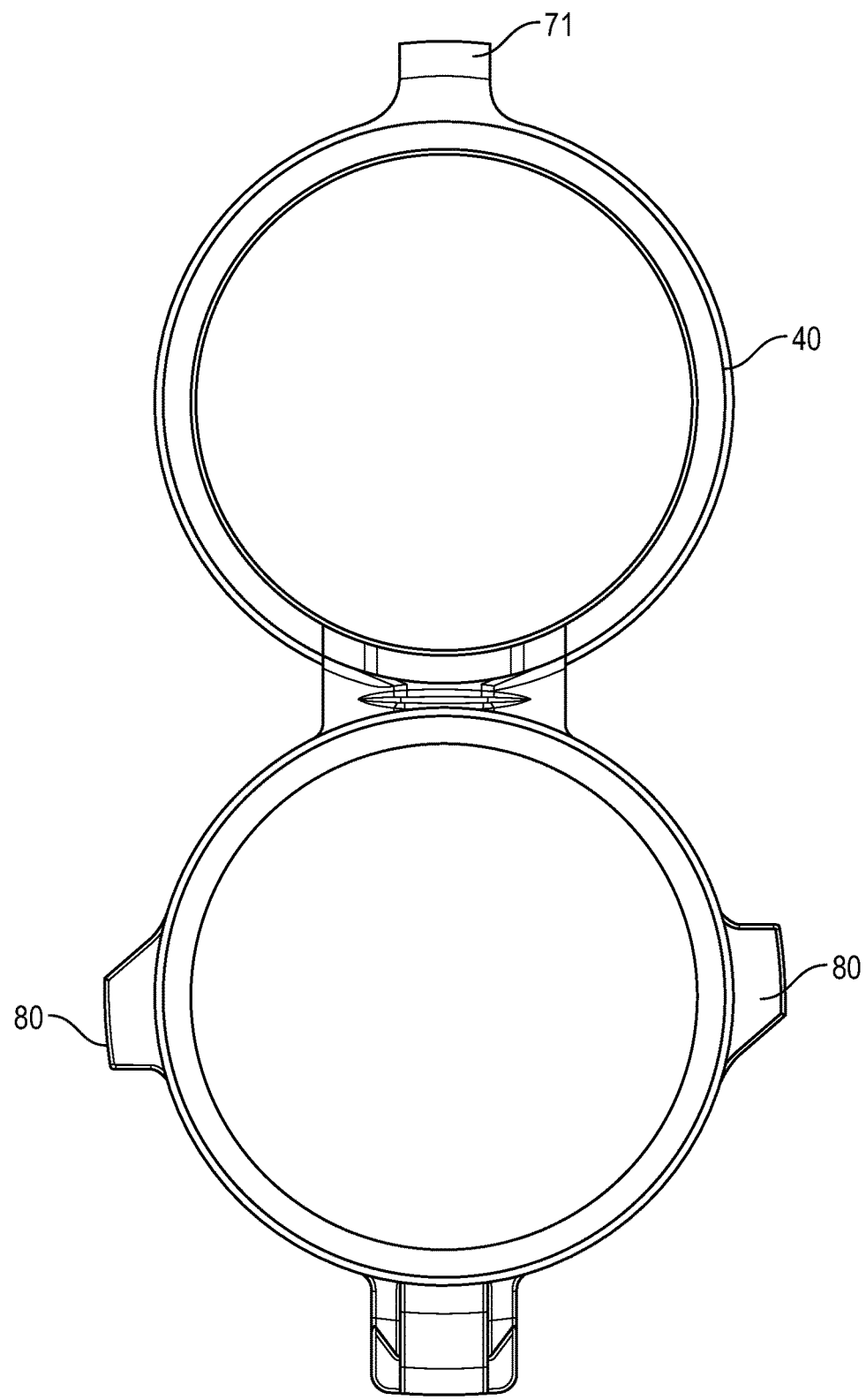
FIG. 10 illustrates a top view of a syringe assembly with a collar, a ring and a cap in an open position in accordance with one or more embodiments of the present disclosure.

In one or more embodiments, the structure for automatically locking the cap 40 in a tip protecting position includes, at least one locking element 70 projecting from the exterior surface of the ring. In one or more embodiments, locking element 70 may be in the form of an arm. The arm includes a free end positioned so that when the cap 40 is pivoted to the closed position, the free end of the arm engages a corresponding mating locking projection 71 on the exterior surface of the collar. As shown in FIG. 2, locking element 70 may include a thumb turn handle 80 to assist in turning the locking element to disengage the free end of the arm of locking element 70 from the corresponding mating locking projection 71 on the exterior surface of the collar In one or more embodiments, as seen in FIG. 8, a slanted surface 90 is disposed with one or more ribs 92 on the top surface of the cap 40 that improves grip. The inside surface of the cap 40 has an outwardly extending protrusion 100 that blocks off the luer tip and prevents leakage when cap is closed. In one or more embodiments, protrusion 100 may be in the shape of a pin or button, as seen in FIGS. 6-8.

In one or more embodiments, a cap 40 is attached to the collar 30 via a hinge 50. FIG. 6 illustrates a partial perspective view of a flush syringe with a hinge 50 connecting the collar 30 and cap 40 in accordance with one or more embodiments of the present disclosure. In one or more embodiments, the hinge is a living hinge. In one or more embodiments, cap 40 is a flip open cap. In one or more embodiments, cap 40 includes a side wall defining a longitudinal opening and a top wall between the side walls defining a recess having an interior surface. The cap is capable of pivoting from an open position wherein the elongated tip 23 is exposed to a closed protecting position wherein the distal end of the elongated tip 23 is within the longitudinal opening of the cap. In one or more embodiments, the collar 30 and the cap 40 can be molded together and then assembled with the barrel 20. In an alternate embodiment, the collar 30 and the syringe barrel 20 are molded together and the cap 40 gets attached to the assembly.

Figure 11:
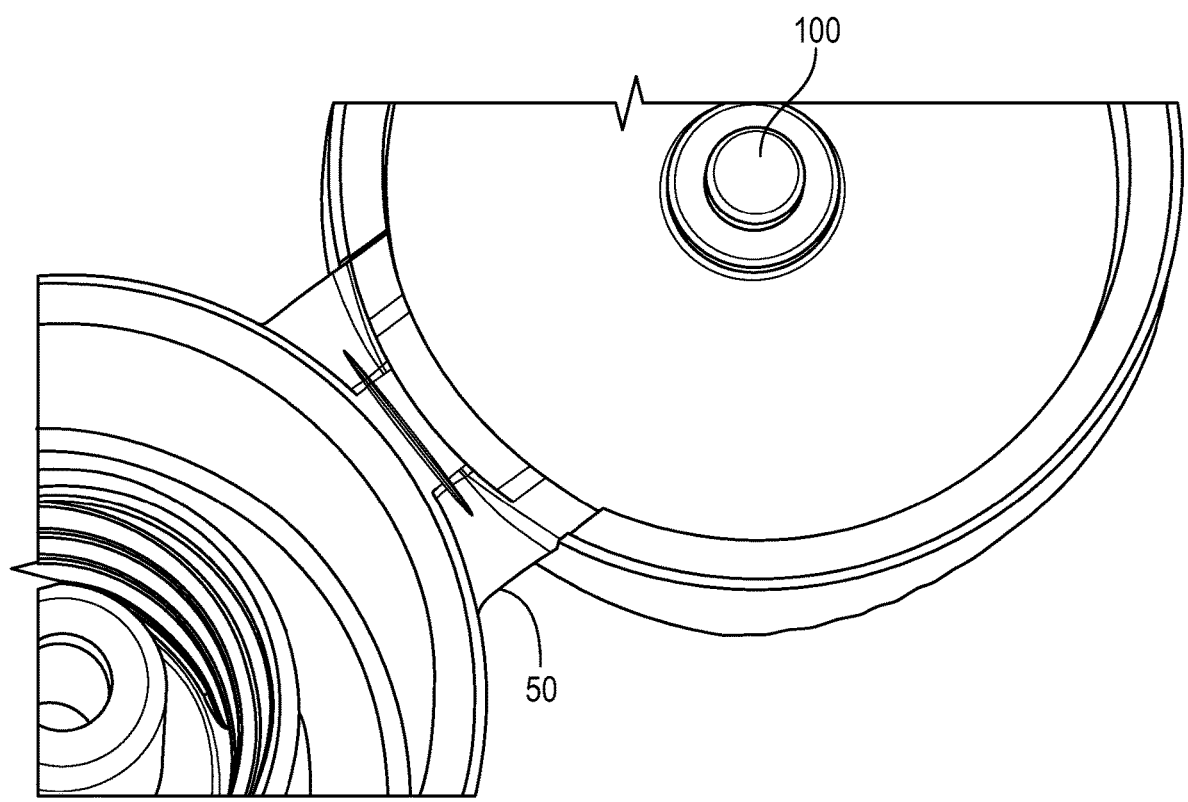
FIG. 11 illustrates a partial perspective view of a flush syringe with a collar, hinge and a cap in accordance with one or more embodiments of the present disclosure.
Figure 12:
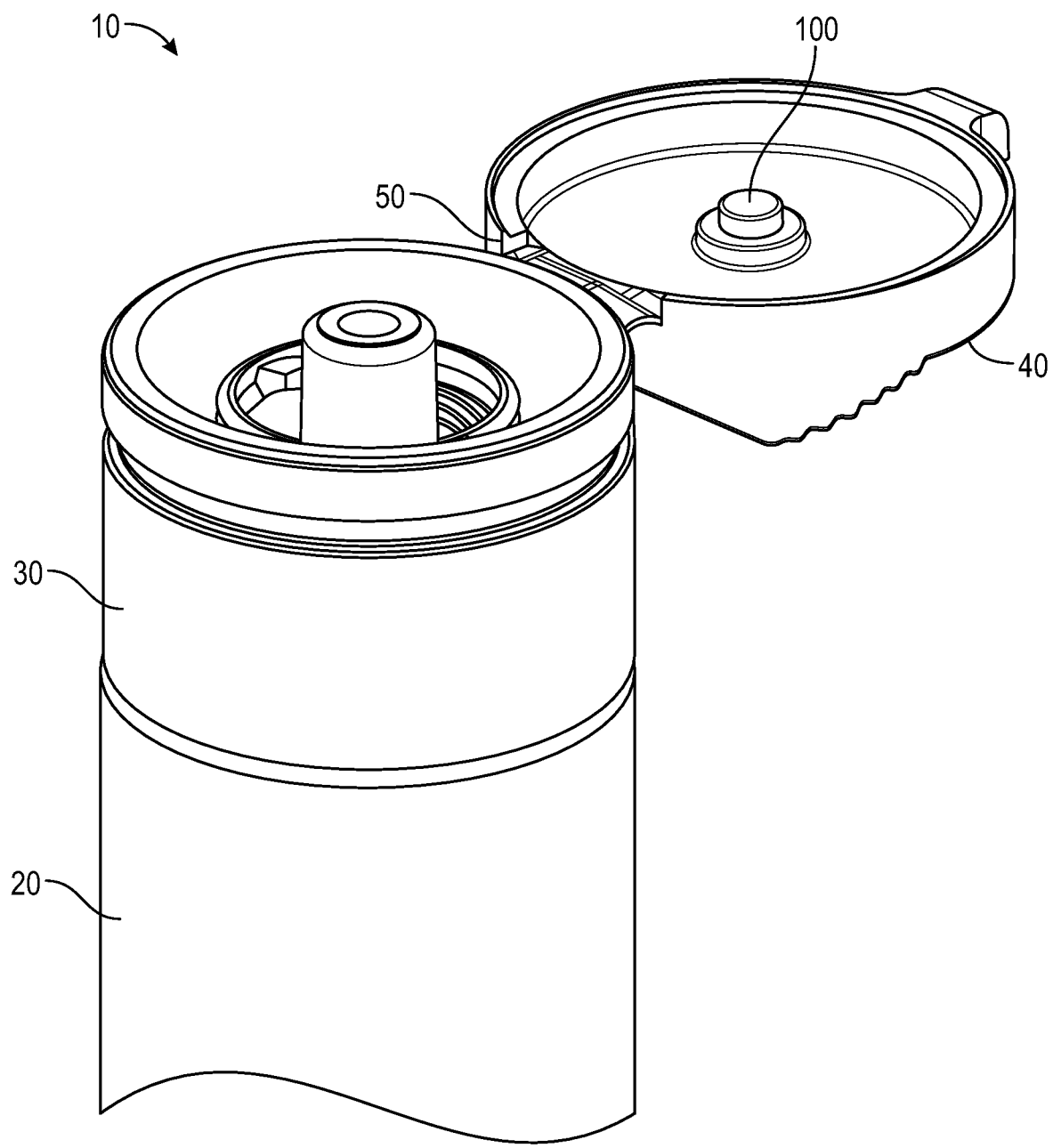
FIG. 12 illustrates a perspective view of a flush syringe with a collar and a cap in an open position without a ring in accordance with one or more embodiments of the present disclosure.
Figure 13:
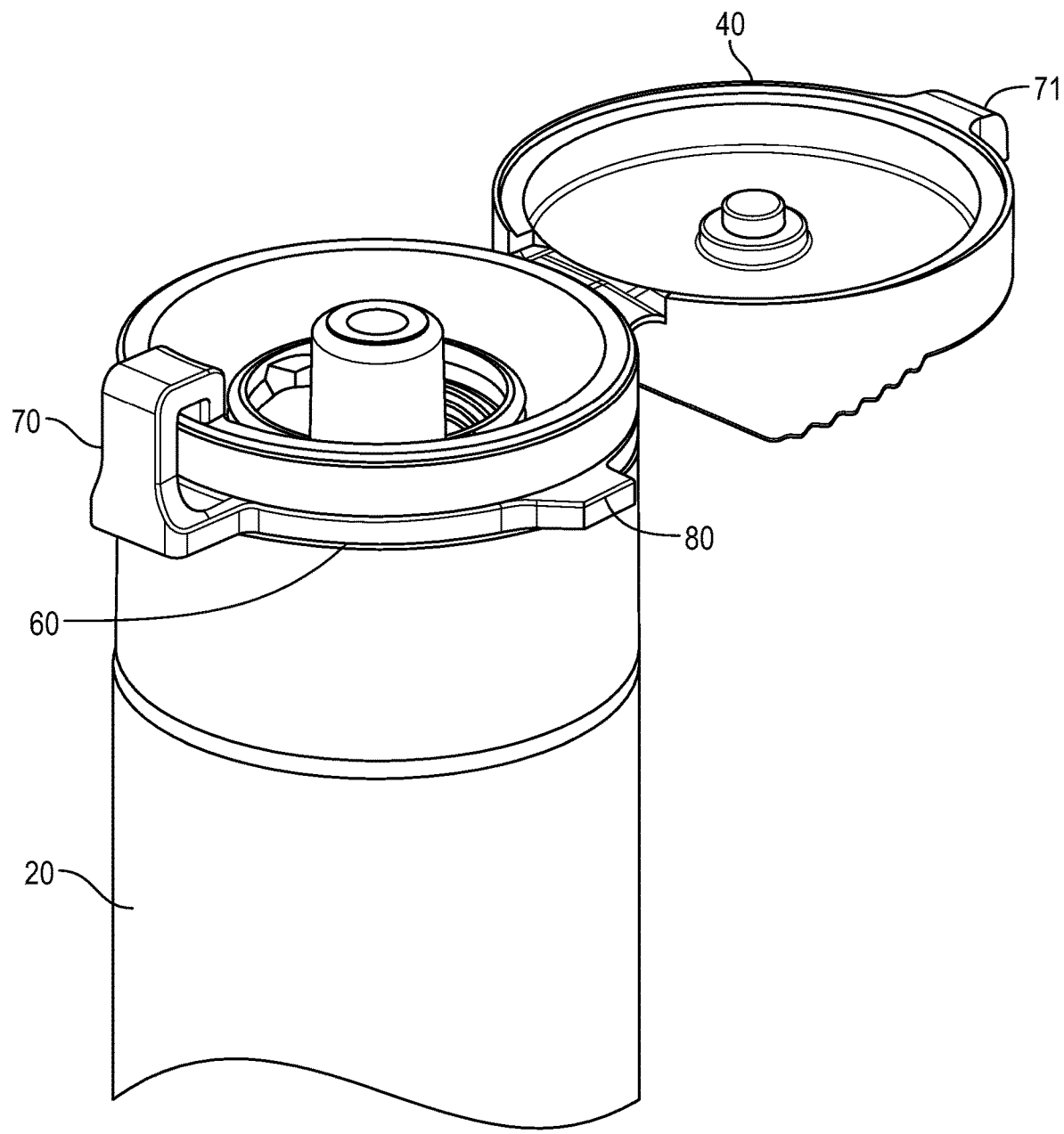
FIG. 13 illustrates a perspective view of a flush syringe with a collar and a cap in an open position with a ring in accordance with one or more embodiments of the present disclosure.

The outwardly extending protrusion 100 prevents leakage after the syringe is filled and the cap 40 is closed until the cap 40 is opened prior to use. In one or more embodiments, the outwardly extending protrusion or pin may be orientated, configured and/or shaped to allow the protrusion to enter the opening at the distal end of the elongated tip, as seen in FIGS. 11-13.

Figure 14:
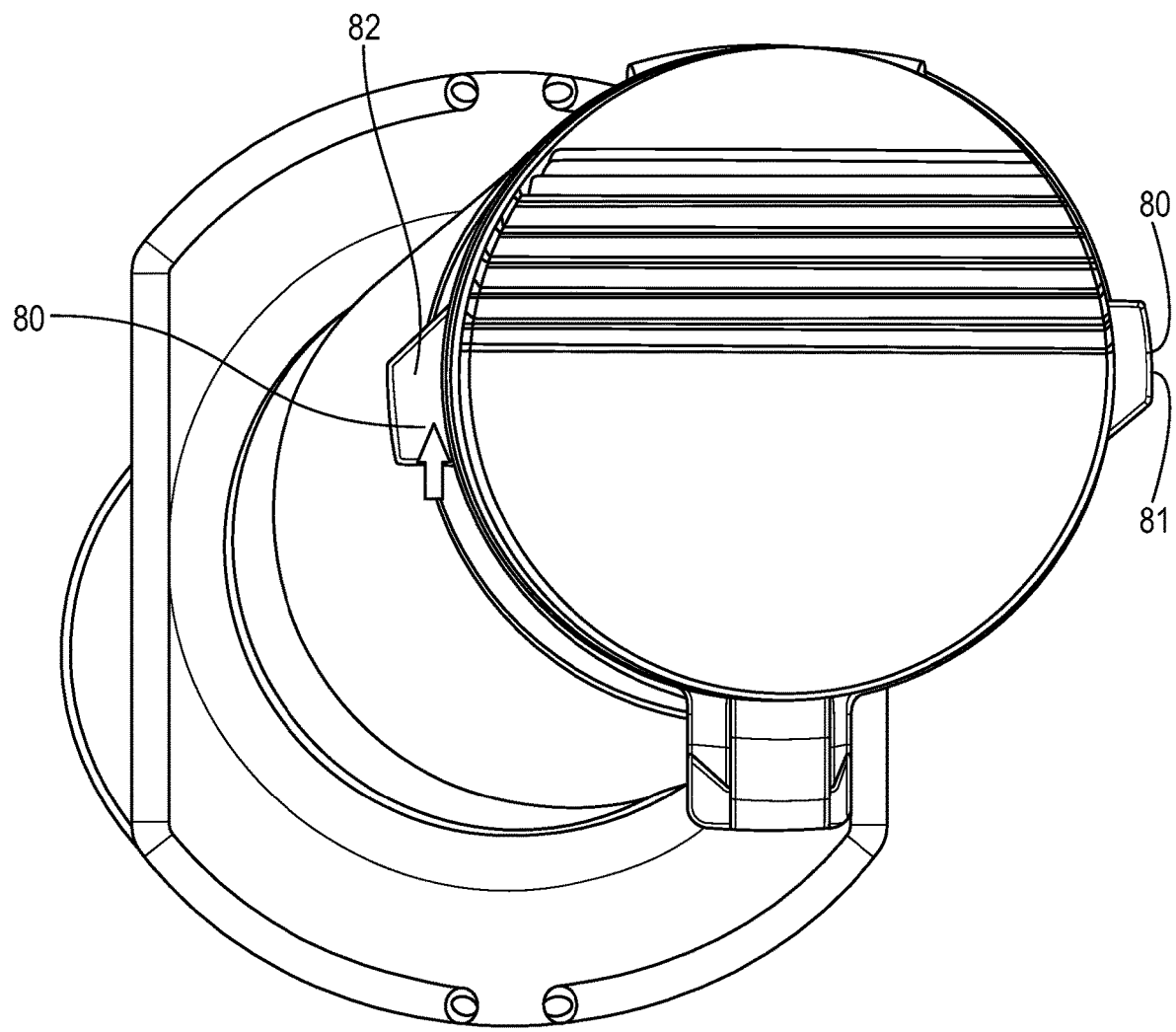
FIG. 14 illustrates a top view of a flush syringe with a collar, a ring and a cap in a closed position accordance with one or more embodiments of the present disclosure.
Figure 15:
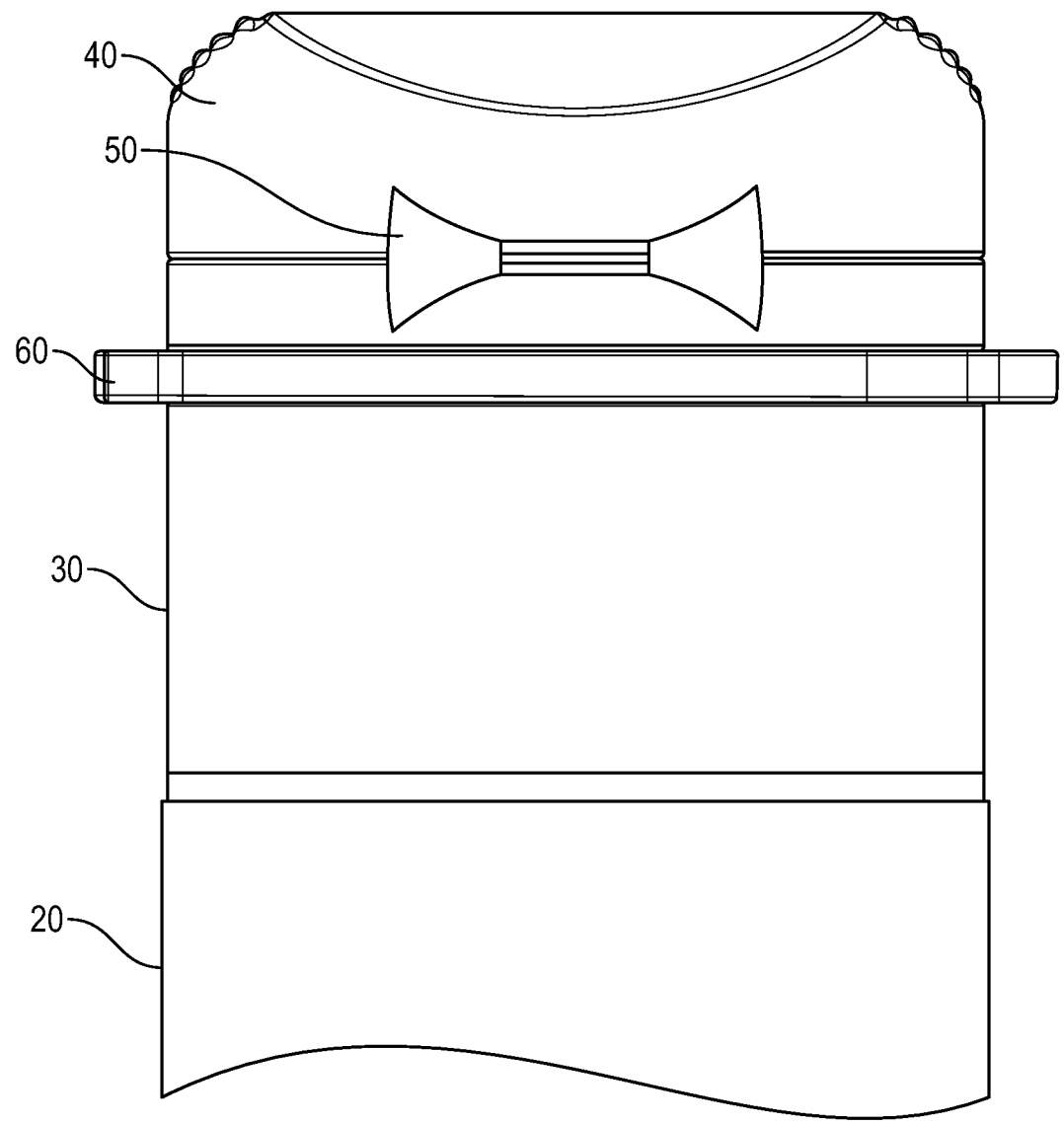
FIG. 15 illustrates a back view of a flush syringe with a collar, a ring and a cap in a closed position accordance with one or more embodiments of the present disclosure.
Figure 16:
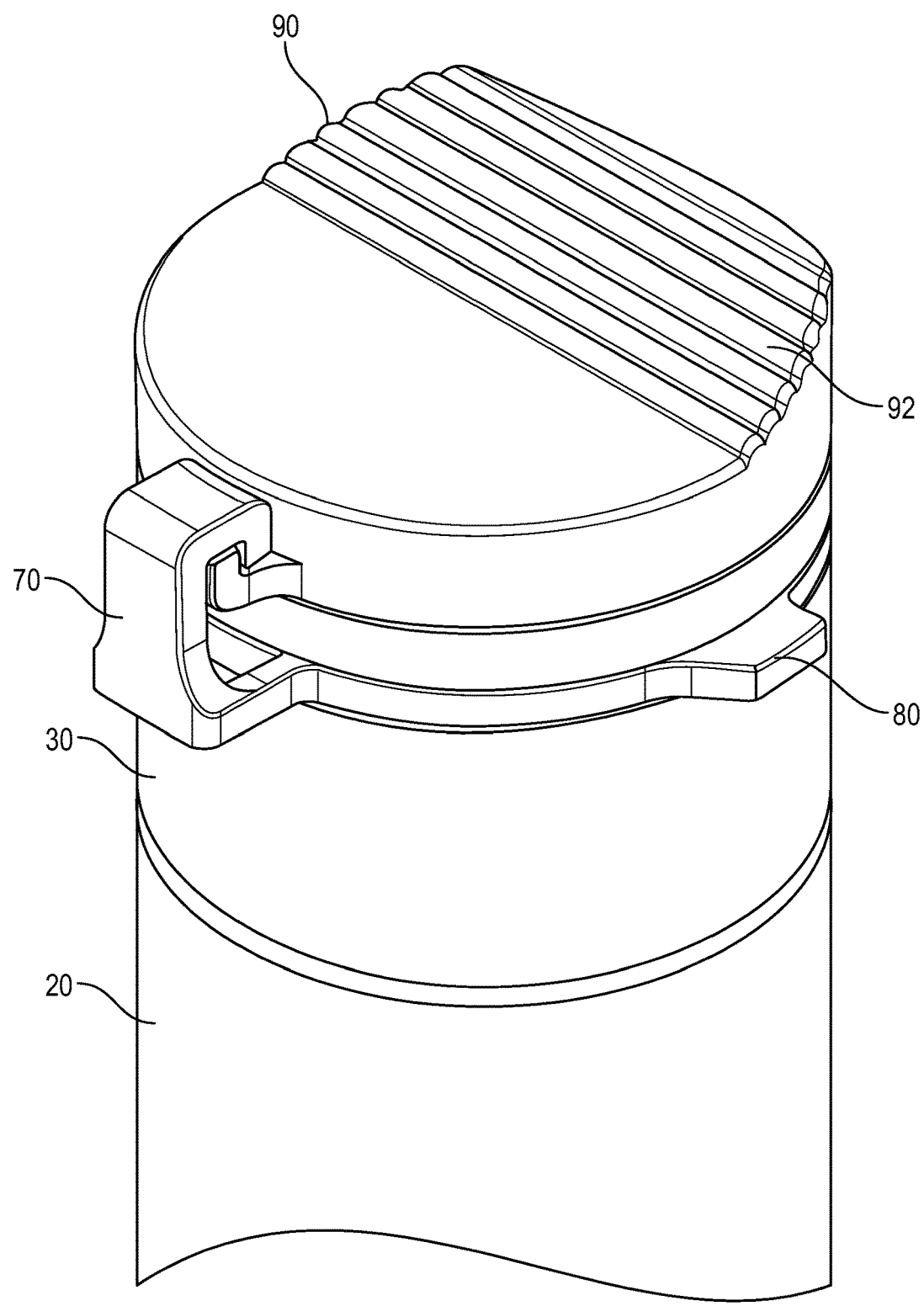
FIG. 16 illustrates a perspective view of a flush syringe with a collar, a ring and a cap in a closed position accordance with one or more embodiments of the present disclosure.
Figure 17A:
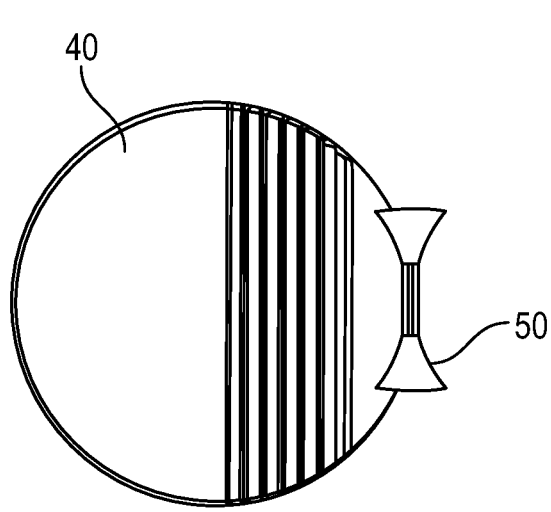
FIG. 17A illustrates a top view of a cap with a butterfly hinge in accordance with one or more embodiments of the present disclosure.
Figure 17B:
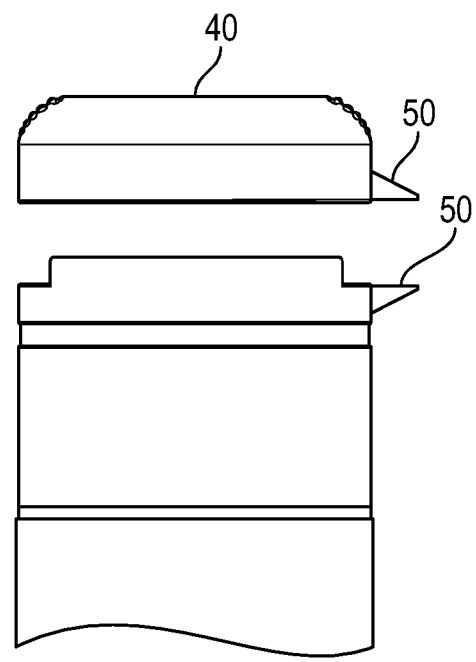
FIG. 17B illustrates an exploded side view of a syringe assembly with a butterfly hinge in accordance with one or more embodiments of the present disclosure.
Figure 17C:
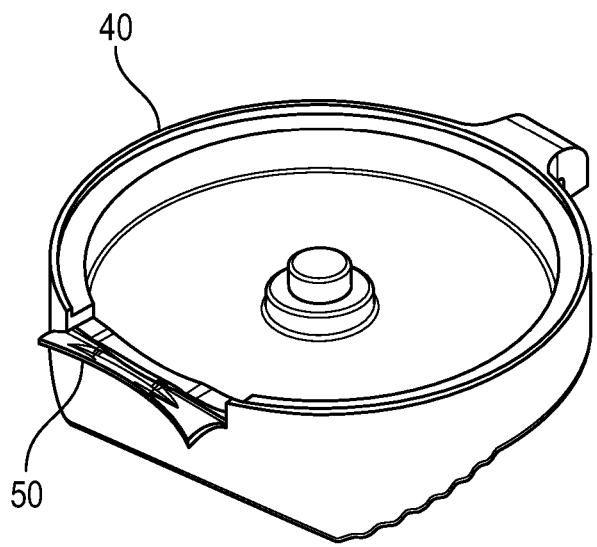
FIG. 17C illustrates a perspective view of an inside of the cap with a protrusion and butterfly hinge in accordance with one or more embodiments of the present disclosure.
Figure 17D:
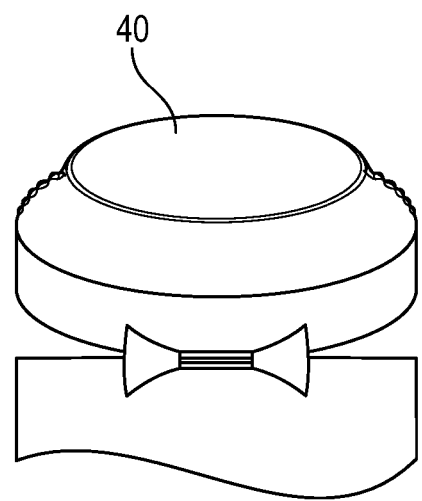
FIG. 17D illustrates a rear view of a syringe assembly with a butterfly hinge in accordance with one or more embodiments of the present disclosure.

As shown in FIG. 14, in one or more embodiments, thumb turn handle 80 may comprise two or more two thumb supports (81, 82) for turning the collar. In the exemplary embodiment shown in FIG. 14, thumb support 81 is configured for a one for right handed clinicians and thumb support 82 is configured for a left-handed clinicians.

The hinge 50 functions such that once the hinge 50 is opened, it remains in place. In one or more embodiments, as shown in FIGS. 17A through 17D, the hinge 50 has a butterfly shape with a central section that serves as a hinge and the two wings on the sides to make it snap into place. In one or more embodiments, the side profile of the central section is a triangular.

Figure 18A:
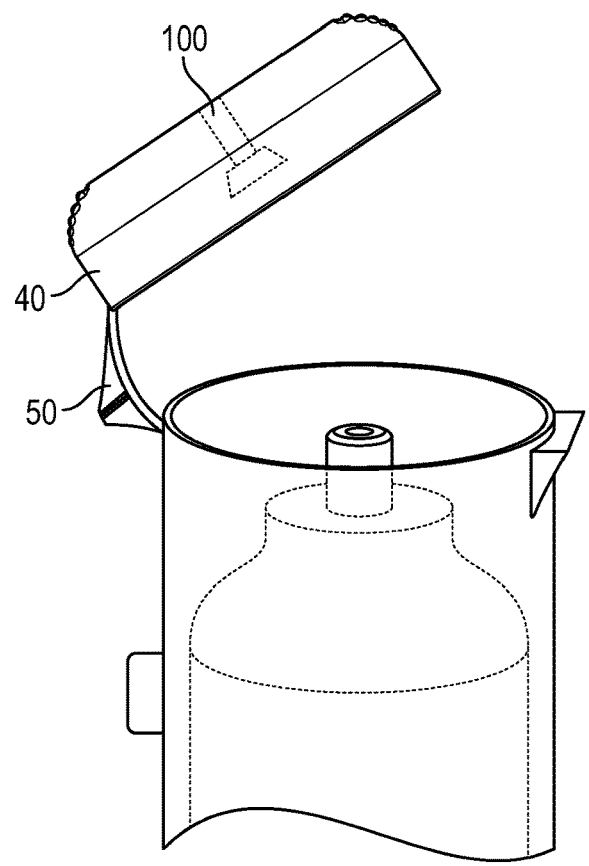
FIG. 18A illustrates a view of a cap of the syringe assembly with a protrusion in the shape of an umbrella pin blocking the elongated tip in accordance with one or more embodiments of the present disclosure.
Figure 18B:
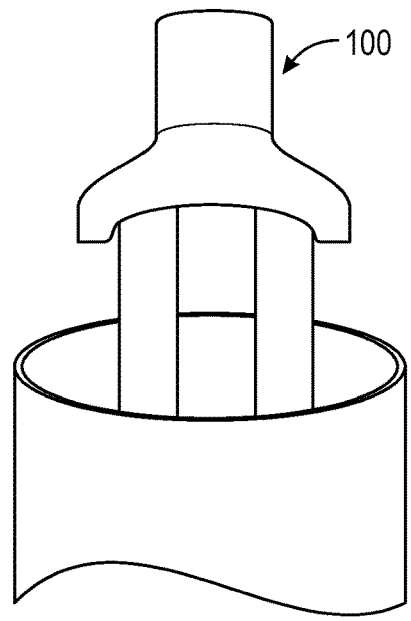
FIG. 18B illustrates a partial view of a protrusion shown in FIG. 18A in the shape of an umbrella pin blocking the elongated tip in accordance with one or more embodiments of the present disclosure.

The inside surface of the cap 40 has an outwardly extending protrusion 100 that blocks off the luer tip and prevents leakage when cap is closed. In one or more alternate embodiments, as seen in FIG. 18 the outwardly extending protrusion 100 may be shaped to resemble a small umbrella, whereby the protrusion 100 forms an arc on the outside of the top part of the distal end of the elongated tip. As shown in FIG. 18, the central part of the outwardly extending protrusion 100 is flat contacting the inner part of a top surface of a corresponding syringe tip and the outer edges are flared or curved downward to enclose the top surface of a corresponding syringe tip which may have a stepped curvature. As shown in FIGS. 18A and 18B, one or more embodiments of cap 40 may include a protrusion 100 in the shape of an umbrella pin blocking the elongated tip.

Figure 19A:
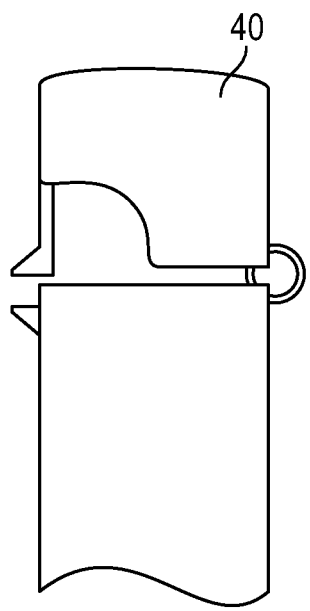
FIG. 19A illustrates a side view of a flush syringe with a spring loaded hinge in accordance with one or more embodiments of the present disclosure.
Figure 19B:
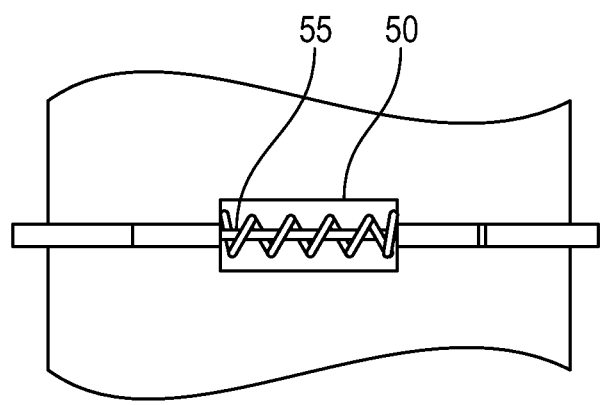
FIG. 19B illustrates a perspective view of a spring loaded hinge as shown in FIG. 19A in accordance with one or more embodiments of the present disclosure.

As shown in FIGS. 19A and 19B, in one or more embodiments, hinge 50 can also be spring loaded, where the pre-tension of a spring 55 is adjusted such that once the cap 40 is popped open, the hinge 50 opens to the required degree. In one more embodiments, the hinge in combination with the spring element forms a hinge assembly. In one or more embodiments, the spring element may include a first segment and a second segment aligned or compressed with respect to one and other in an initial closed cap condition. However, first and second segments of spring element can be resiliently deflected by the resiliency inherent in spring element to urge the cap to an open position. The self-propelling attributes of the hinge in combination with the spring element are desirable to facilitate one-hand operation of the needle. The accumulated energy of the spring performs work for the user by urging the cap toward the open position to expose the elongated tip. Spring element 55 will, preferably, be stable with, preferably, little or no stored energy while in the open position. Hinge 50 which is operated or loaded with spring 55 allows for a cap that may be open to an angle greater than 120°.

In one or more embodiments, the hinge 50 opens between a fully closed position to a fully open position to the required degree of at least 120 degrees.

Other embodiment can additionally include a gasket feature between the collar and the flip open cap to create a tight seal for maintaining sterility, as shown in FIG. 20. In one or more embodiments, the elongated tip may be a luer tip.

Other embodiment can additionally include a gasket feature between the collar and the flip open cap to create a tight seal for maintaining sterility, as shown in FIG. 20. In one or more embodiments, the elongated tip may be a luer tip.

Figure 20A:
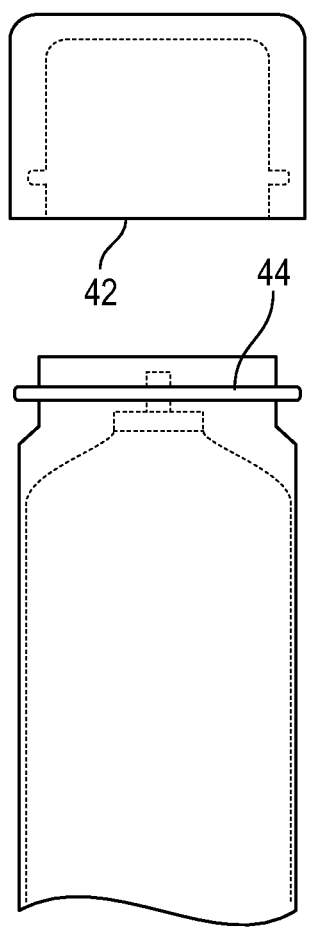
FIG. 20A illustrates a front view of a cap showing a groove feature inside the cap that provides a seal when closed and engaged with the seal ring on the outer surface of the barrel collar in accordance with one or more embodiments of the present disclosure.
Figure 20B:
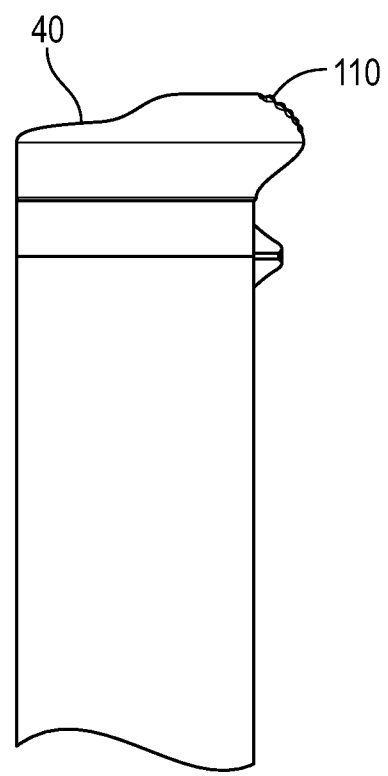
FIG. 20B illustrates a side view of a cap showing a groove feature inside the cap that provides a seal when closed and engaged with the seal ring on the outer surface of the barrel collar in accordance with one or more embodiments of the present disclosure.

As shown in FIGS. 20A and 20B, in one or more embodiments, the cap opens in two steps, wherein a first step, the cap gets pushed up to disengage the ring and groove features by the user pushing up with the thumb on 'Surface A'. In the second step, the cap is flipped backwards from the initial position by pushing up with the thumb on 'Surface A'. In one or more embodiments, there is no need to reposition the thumb.

In one or more embodiments, Surface A has surface texture to improve friction with the thumb of a user. In one or more embodiments, as shown in FIG. 20, finger grips 110 may be incorporated on an outside surface of the cap. In one or more embodiments, the finger grips 110 may be fabricated from a suitable elastomer.

In one or more embodiments, the cap 40 is both easy to open by flipping it backwards (the thumb of the user moving away from the elongated tip 23) and the cap is also sufficiently tight to provide minimum sterility assurance levels. The two-step opening process enables the user to disengage the tight seal in one step and allows easy removal of the cap, as the cap is designed to prevent the need for repositioning of the user's thumb between the two steps.

In one or more alternate embodiments, as shown in FIG. 20, the cap 40 can have more than one ring-groove set features (e.g. two consecutive rings). As shown in FIG. 20, Feature B is an element that keeps the cap attached to the barrel after opening. As shown in FIG. 20, a groove 42 is disposed on the inside of the cap that provides a seal when closed and engaged with the seal ring 44 on the outer surface of the barrel collar.

Figure 21:
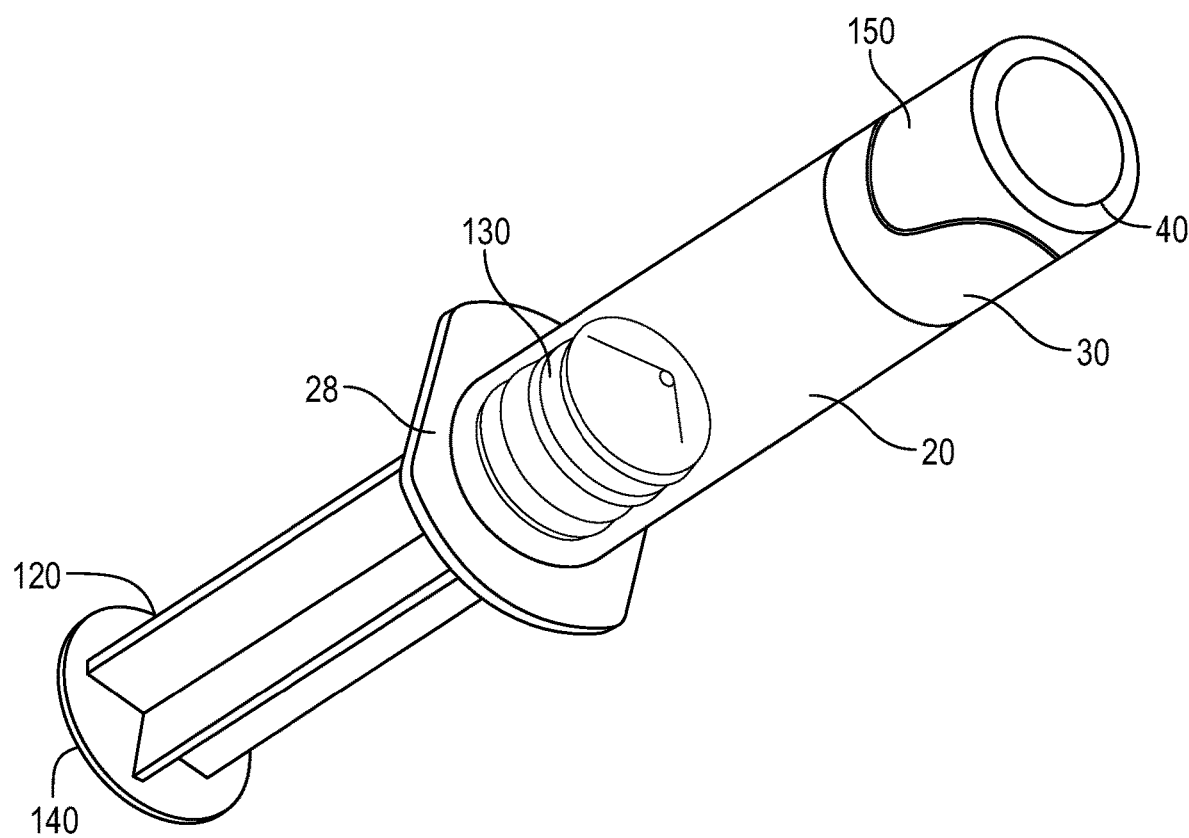
FIG. 21 illustrates a perspective view of a flush syringe with a collar and a cap in a closed position accordance with one or more embodiments of the present disclosure.

In one or more embodiments, as shown in FIG. 21, a skirt 150 may extend in a perpendicular direction from the top surface of the cap 40 and is dimensioned for sealing engagement with the collar.

The syringe, cap and collar may be fabricated from suitable medical grade materials including polymers or metals. Preferably the caps are injection-molded using a thermoplastic and/or thermoplastic elastomer (TPE).

In one or more embodiments, the shape of the collar 30 can vary. Collar 30 may have shapes including, but not limited to, circular, oval, a convex inner surface (for example a paraboloid), concave inner surface, with a straight profile (i.e., semi conical shape), or have the shape of a trapezoidal prism. The length of this extension from the main body of syringe and the degree of openness/straightness of the profile (how wide the collar is at the end farthest from the syringe barrel) can vary.

In one or more embodiments, the collar 30 surrounds an elongate tip 23 adapted for connection to the hub of the vascular access devices. In one or more embodiments, the elongate tip is a Luer tip.

Cap 40 may comprises an outward protrusion 100 that extends from the body of the cap 40 and corresponds with the opening of the distal end of the elongate tip 26.

The cross-sectional shape of the cap 40 can be any suitable shape including, but not limited to, circular, oval, triangular, square, pentagonal, hexagonal, heptagonal, octagonal, symmetric or non-symmetric polygonal. The shape of the cap 40 can provide a comfortable feel for the user and enhanced gripping ability to allow the user to easily open the cap from the locking element 70 and corresponding mating locking projection 71.

The syringe assembly 10 may be filled with flush solution using known methods. Additionally, the syringe assembly 10 may be provided pre-filled from the manufacturer or supplier. The flush solution may be any solution intended for flushing or maintaining performance of VAD's. It is preferred that the flush solution be selected from the group consisting of saline flush solution and heparin lock flush solution. These solutions are known in the art and are readily available. An example of a saline flush solution includes, but is not limited to, 0.9% sodium chloride USP for injection. An example of a heparin lock flush solution includes but is not limited to 0.9% sodium chloride with 100 USP units of heparin sodium per mL or 10 USP units of heparin sodium per mL.

Once the connection of the syringe assembly 10 to the VAD is completed, fluid communication from the barrel 20 of the syringe to the vascular access device can occur. Fluid is drawn from the barrel 20 through the integral passageway 27 into the IV or catheter. Because of the presence of the collar 30, fluid communication through a vascular access device and into a patient is conducted under aseptic conditions without any additional swabbing steps and diligence on the part of the clinician.

In one or more embodiments, the collar 30 can be integrally formed on the distal wall 25 of the syringe barrel 20 for fluid communication to the vascular access device.

The barrel may also include a tip 23 which extends distally from the barrel. The tip can have an outer diameter that is different from or the same as the outer diameter of the rest of the barrel. For example, as shown in the Figures, the outer diameter of the tip has a smaller outer diameter than the barrel portion that is proximal of the tip. The tip of the barrel may include a luer slip connection or a locking luer type collar concentrically surrounding the tip or within the tip.

As shown in FIG. 21, an elongated plunger rod 120 may include a distal portion and a proximal portion, the plunger rod further comprising a distal end including a stopper 130 slidably positioned in fluid-tight engagement with the inside surface of the barrel for drawing fluid into and driving fluid out of the chamber by movement of the stopper relative to the barrel, the elongated plunger rod extending outwardly from the open proximal end 28 of the barrel 20, the stopper having a distal surface.

An elongate plunger rod may be disposed within the barrel 20. The plunger rod 120 includes an elongate body portion with a proximal end and a distal end.

The elongate body portion of the plunger rod has an axial length extending from the proximal end to the distal end. The body portion may include a single beam or features, which may have cylindrical or other shapes. The body portion may be formed by two perpendicularly intersecting beams.

The plunger rod may also include a thumb press 140 at the proximal end of the elongate body portion. The shape of the thumbpress can vary depending on the desired usage of the flush syringe assembly. The shape of the thumb press may be round, square, rectangular, triangular, oval, pentagonal, hexagonal and cruciform.

A stopper 130 can be connected to the distal end of the plunger rod. The shape and size of the stopper can be any suitable shape or size depending on, for example, the shape and size of the barrel and plunger rod. The plunger rod is slidably positioned in the barrel so that the stopper is in fluid-tight contact with the inside surface of the barrel and so that distal movement of the plunger rod relative to the barrel causes the stopper to push the fluid out of the barrel. In some embodiments, the stopper is slidably positioned in fluid-tight contact with the inside surface of the barrel for driving fluid out of the chamber by movement of the stopper relative to the barrel. The stopper can be connected to the distal end of the elongate plunger rod by any suitable means. In some embodiments, the stopper is connected by a mechanical connection such as interaction of complementary screw threads and press-fit connections. The stopper may be slidably positioned in fluid-tight engagement with the inside surface of the barrel for drawing fluid into and driving fluid out of the chamber.

The stopper may be made of any material suitable for providing a seal with the inside surface of the barrel. For example, the stopper may be made of thermoplastic elastomers, natural rubber, synthetic rubber or thermoplastic materials and combinations thereof. The stopper may be integrally formed or composed of separate components of the same or different materials joined together. The plunger rod may be made of material which is more rigid than the stopper such as polypropylene, polyethylene and the like. Materials should be chosen to be compatible with the procedure being used.

FIG. 21. illustrates a perspective view of a flush syringe with a collar and a cap in a closed position accordance with one or more embodiments of the present disclosure. As shown in FIG. 21, also provided are syringe assemblies that include a plunger rod and a syringe barrel having an open proximal end and a distal tip, the distal syringe tip surrounded by a collar to facilitate alignment of the syringe with a catheter hub or needle-free connector, as well as, reducing contamination of the syringe by preventing contact of the syringe tip with the surrounding non-sterile environment.

Figure 22:
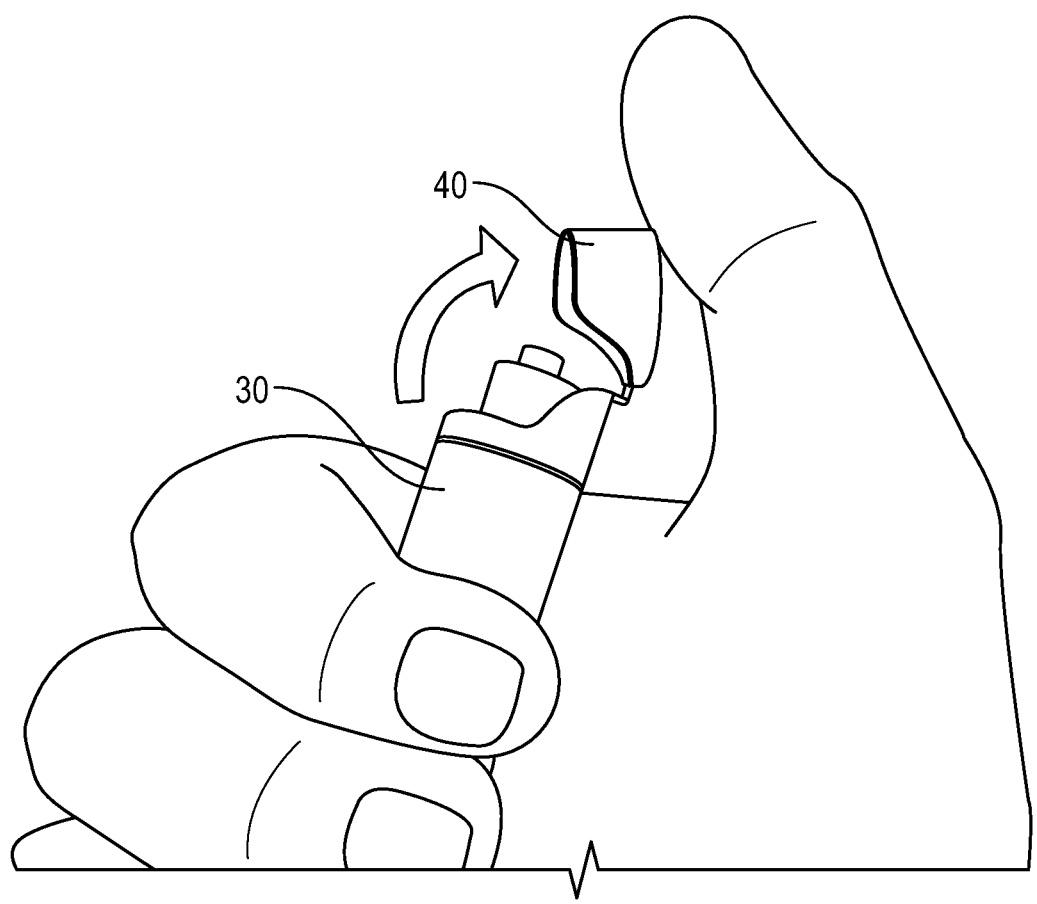
FIG. 22 illustrates a perspective view of a flush syringe with a collar and a cap in an open position accordance with one or more embodiments of the present disclosure.

FIG. 22 illustrates a perspective view of a flush syringe with a collar and a cap in an open position accordance with one or more embodiments of the present disclosure.

Figure 23:
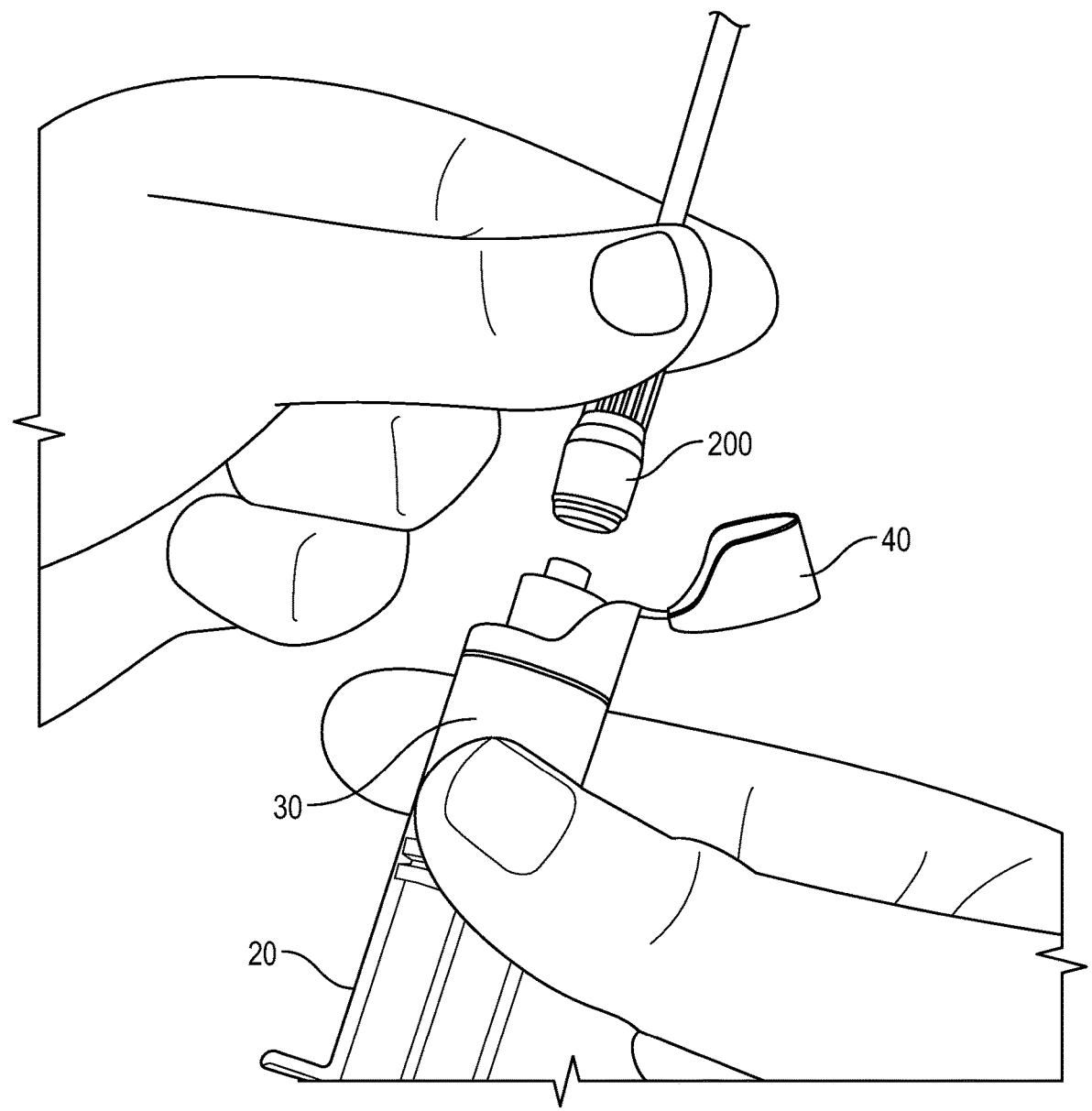
FIG. 23 illustrates a perspective view of a flush syringe with a collar and a cap in an open position attached to a vascular access device in accordance with one or more embodiments of the present disclosure.

FIG. 23 illustrates a perspective view of a flush syringe with a collar and a cap in an open position attached to a vascular access device 200 in accordance with one or more embodiments of the present disclosure.

Figure 24:
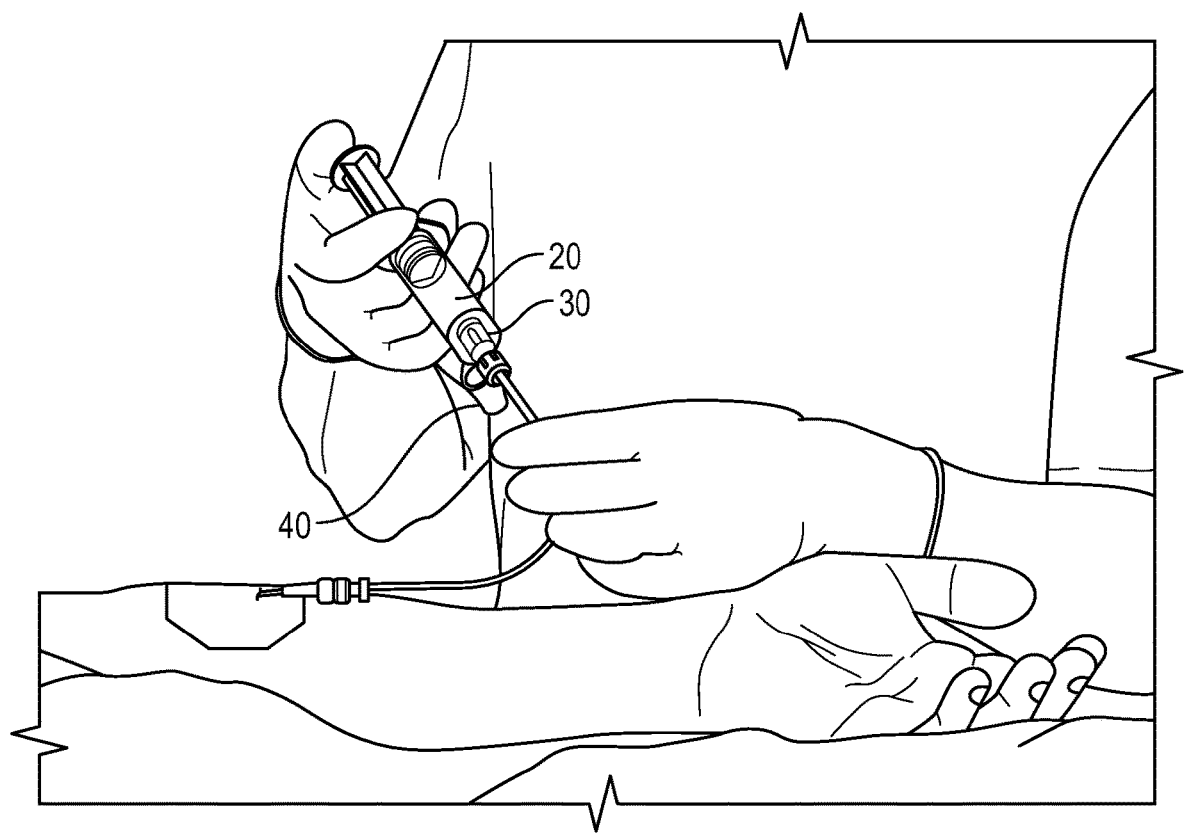
FIG. 24 illustrates a perspective view of a flush syringe with a collar and a cap in use accordance with one or more embodiments of the present disclosure.

FIG. 24 illustrates a perspective view of a flush syringe with a collar and a cap in use in accordance with one or more embodiments of the present disclosure.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as disclosed.

What is claimed is:

1. A flush syringe assembly comprising:
    a barrel including a chamber for retaining a fluid, an open proximal end, a distal end including a distal wall with an elongate tip extending therefrom having a passageway therethrough in fluid communication with said chamber;
    a collar mounted on the distal wall of the barrel and surrounding the elongate tip, the collar including a compartment, an open distal end, and a proximal end adjacent the distal wall of the barrel;
    a cap attached to the collar via a hinge, wherein the cap includes protrusion that interacts with the elongate tip, a groove disposed on an inside of the cap configured to that engage with a seal of the collar, and a skirt extending in a perpendicular direction from the cap, the skirt dimensioned for sealing engagement with the collar;

a gasket is disposed between the collar and the cap; and an plunger rod disposed within the barrel, the plunger rod comprising a rod distal end and a rod proximal end, the rod distal end including a stopper slidably positioned in fluid-tight engagement with an inside surface of the barrel for drawing fluid into and driving fluid out of the chamber by movement of the stopper relative to the barrel, the plunger rod extending from the open proximal end of the barrel.

2. The flush syringe assembly of claim 1, wherein the compartment of the collar surrounds the elongated tip.

3. The flush syringe assembly of claim 1, wherein the hinge is a living hinge.

4. The flush syringe assembly of claim 1, wherein the hinge is a butterfly shape with a central hinge section and two lateral wings.

5. The flush syringe assembly of claim 1, wherein the hinge is spring loaded.

6. The flush syringe assembly of claim 5, wherein the hinge opens between a fully closed position to a fully open position of at least 120 degrees.

7. The flush syringe assembly of claim 1, wherein the protrusion has a flat central part and flared or curved downward outer edges.

8. The flush syringe assembly of claim 1, wherein the protrusion is button-shaped.

9. The flush syringe assembly of claim 1, wherein the protrusion is pin-shaped.

10. The flush syringe assembly of claim 1, wherein the protrusion is umbrella-shaped.

11. The flush syringe assembly of claim 1, wherein the cap includes a slanted surface.

12. The flush syringe assembly of claim 11, wherein the slanted surface includes one or more ribs.

13. The flush syringe assembly of claim 12, wherein the one or more ribs are made of an elastomeric material.

14. The flush syringe assembly of claim 11, wherein at least a portion of the cap is made of an elastomeric material.

15. The flush syringe assembly of claim 1 further comprising a second groove disposed on an inside of the cap and second seal around the collar.

16. The flush syringe assembly of claim 1, further comprising a locking element.

17. The flush syringe assembly of claim 1, wherein the elongate tip is formed to couple with a needle-free connector.

18. The flush syringe assembly of claim 17, wherein the needle-free connector is a luer connector.

* * * * *